(12) United States Patent
Hoggarth, Jr. et al.

(10) Patent No.: US 11,883,317 B2
(45) Date of Patent: Jan. 30, 2024

(54) OSTOMY APPLIANCE

(71) Applicant: ConvaTec Limited, Flintshire (GB)

(72) Inventors: Marcus Hoggarth, Jr., London (GB); Oliver Poyntz, London (GB)

(73) Assignee: ConvaTec Limited, Flintshire (GB)

( * ) Notice: Subject to any disclaimer, the term of this patent is extended or adjusted under 35 U.S.C. 154(b) by 0 days.

(21) Appl. No.: 17/943,273

(22) Filed: Sep. 13, 2022

(65) Prior Publication Data
US 2023/0074823 A1    Mar. 9, 2023

Related U.S. Application Data

(63) Continuation of application No. PCT/GB2021/050895, filed on Apr. 14, 2021.

(30) Foreign Application Priority Data

| Apr. 15, 2020 | (GB) | 2005463 |
| Apr. 15, 2020 | (GB) | 2005464 |
| Apr. 15, 2020 | (GB) | 2005465 |

(51) Int. Cl.
*A61F 5/441* (2006.01)
*A61F 5/445* (2006.01)
(Continued)

(52) U.S. Cl.
CPC ............ *A61F 5/441* (2013.01); *A61F 5/4405* (2013.01); *A61F 5/445* (2013.01); *A61F 5/448* (2013.01)

(58) Field of Classification Search
CPC ........ A61F 5/441; A61F 5/445; A61F 5/4405; A61F 5/448
See application file for complete search history.

(56) References Cited

U.S. PATENT DOCUMENTS

| 3,902,496 A | 9/1975 | Eakin |
| 5,074,851 A * | 12/1991 | Plass ...................... A61F 5/441 |
| | | 55/385.4 |

(Continued)

FOREIGN PATENT DOCUMENTS

| DE | 19750545 A1 * | 5/1999 | ............. A61F 5/441 |
| DE | 19750545 A1 | 5/1999 | |

(Continued)

OTHER PUBLICATIONS

International Search Report for International Application No. PCT/GB2021/050895; dated Nov. 30, 2021; 5 paged.

*Primary Examiner* — Guy K Townsend
(74) *Attorney, Agent, or Firm* — Taft Stettinius & Hollister LLP; Ryan O. White; Derek B. Lavender

(57) ABSTRACT

An ostomy appliance having an appliance wall of flexible sheet material forming a cavity for containing a stomal output. The wall has a stomal inlet for receiving the stomal output and a gas vent for allowing the stomal gas to migrate out of the cavity. A filter arrangement is mounted to the appliance wall and has a filter channel extending from a filter channel inlet to a filter channel outlet. The filter channel inlet is located in the cavity for receiving the stomal output from the cavity and the filter channel outlet is mounted in communication with the gas vent for allowing stomal gas to migrate out of the filter channel to the gas vent. A separation element extends along the filter channel for maintaining the filter channel in an open configuration along part of the filter channel for allowing stomal gas to pass therethough.

18 Claims, 19 Drawing Sheets

(51) Int. Cl.
*A61F 5/448* (2006.01)
*A61F 5/44* (2006.01)

(56) References Cited

U.S. PATENT DOCUMENTS

| | | | | |
|---|---|---|---|---|
| 5,250,042 | A * | 10/1993 | Torgalkar | A61F 5/441 604/339 |
| 5,306,264 | A * | 4/1994 | Ferguson | A61F 5/441 604/338 |
| 5,401,264 | A * | 3/1995 | Leise, Jr. | A61F 5/441 604/333 |
| 5,643,234 | A * | 7/1997 | Lesko | A61F 5/441 604/338 |
| 6,712,800 | B2 * | 3/2004 | Kanbara | A61F 5/441 604/333 |
| 7,083,569 | B2 * | 8/2006 | Boulanger | A61F 5/445 604/277 |
| 7,214,217 | B2 * | 5/2007 | Pedersen | A61F 5/441 604/338 |
| 7,476,220 | B2 * | 1/2009 | Lillegaard | A61F 5/4405 604/338 |
| 7,572,492 | B2 * | 8/2009 | Bager | B29C 66/472 228/244 |
| 7,604,622 | B2 * | 10/2009 | Pedersen | A61F 5/448 604/338 |
| 8,684,982 | B2 * | 4/2014 | Nguyen-DeMary | A61F 5/441 604/327 |
| 9,707,120 | B2 * | 7/2017 | Nguyen-DeMary | A61F 5/441 |
| 10,285,847 | B2 * | 5/2019 | Lesko | A61F 5/441 |
| 10,478,329 | B2 * | 11/2019 | Oberholtzer | A61F 5/445 |
| 11,166,837 | B2 * | 11/2021 | Lesko | A61F 5/441 |
| 2003/0014023 | A1 * | 1/2003 | Kanbara | A61F 5/441 604/333 |
| 2005/0143696 | A1 * | 6/2005 | Pedersen | A61F 5/448 604/332 |
| 2007/0049880 | A1 * | 3/2007 | Suehr | A61F 5/441 604/333 |
| 2007/0203466 | A1 * | 8/2007 | Pedersen | A61F 5/441 604/339 |
| 2008/0004580 | A1 * | 1/2008 | Mullejans | A61F 5/441 604/344 |
| 2009/0227973 | A1 * | 9/2009 | Worsoee | A61F 5/441 264/299 |
| 2010/0241092 | A1 * | 9/2010 | Nguyen-DeMary | A61F 5/4407 604/336 |
| 2012/0283678 | A1 * | 11/2012 | Nguyen-DeMary | A61F 5/445 604/338 |
| 2013/0072886 | A1 * | 3/2013 | Schertiger | A61F 5/445 604/335 |
| 2013/0085463 | A1 * | 4/2013 | Lesko | A61F 5/441 604/333 |

FOREIGN PATENT DOCUMENTS

| | | | |
|---|---|---|---|
| GB | 2302028 A * | 1/1997 | A61F 5/441 |
| GB | 2302028 A | 1/1997 | |

* cited by examiner

OSTOMY APPLIANCE

CROSS-REFERENCE TO RELATED DISCLOSURES

The present disclosure is a continuation of International Patent Application No. PCT/GB2021/050895 filed on Apr. 14, 2021 and claims the benefit of GB Application Nos. 2005464.9, 2005463.1, and 2005465.6 all filed on Apr. 15, 2020, the contents of which are incorporated herein in entirety.

TECHNICAL FIELD

The present disclosure relates to an ostomy appliance for managing effluent from a stoma and particularly to an ostomy appliance comprising a filter arrangement. The present disclosure further provides a method of manufacturing an ostomy appliance.

BACKGROUND OF THE DISCLOSURE

There are many forms of ostomy appliance which try to provide a secure, comfortable fit for ostomates. However, stomal output gas may accumulate in the ostomy appliance, resulting in the ostomy appliance expanding and increasing the likelihood of the ostomy appliance moving from its original position during use. In addition to forming a visible bulge under the ostomate's clothing, any movement of the ostomy appliance may result in leaking or the ostomy appliance falling off the ostomate. Therefore, the ostomy appliance may include an outlet for the stomal output gas to escape from the ostomy appliance. An odour absorbing gas filter may be employed at the outlet. However, the outlet and/or filter may become blocked and thus expansion of the ostomy appliance may still occur.

U.S. Pat. No. 8,298,201 discloses a filter for an ostomy appliance comprising a pathway for leading gases to a vent in an ostomy bag and a protective element contained in said pathway to prevent solid or semi-liquid waste from blocking the pathway. A channel formed by a liquid impermeable layer defines the pathway and contains a protective element of an open celled compressible material having a memory and a pore size of at least 60 PPI. The protective element extends in the same direction as the gas flow within the channel. The channel has an opening providing access to the pathway from the interior of the bag and the pathway has another opening being connected to a vent in the ostomy bag, optionally via a deodorizing filter.

US-A-2003/0014023 discloses a body waste collector. U.S. Pat. No. 5,250,042 discloses an ostomy bag with a filter combination.

There remains a need for ostomy appliances with enhanced usability for ostomates, particularly in the areas of improved stomal output gas venting and reduced ostomy appliance expansion due to stomal output gas.

SUMMARY OF THE DISCLOSURE

In this specification, the term "stomal output" refers to any gases or fluids or solids produced by an ostomate that may be secreted from the stoma or that exit the stoma. The stomal output may comprise stomal gas, stomal liquid and stomal solids. In this specification, the term "stoma" refers to an opening in the body. Generally the stoma is a surgical opening in the torso of the body. In some instances, the term "stoma" also refers to internal tissue, organs or portions thereof that are exposed by the opening. By way of non-limiting example, internal tissue may be selected from colon, ileum, small intestine, large intestine, jejunum, and duodenum, and combinations thereof. The internal tissue may be an end or a loop of a small or large intestine.

In this specification, the term "ostomate" refers to a subject that may have use of the ostomy appliance disclosed herein. While ostomate usually refers to a subject with a surgical opening, as used herein, "ostomate" may refer to a subject who has a stoma, regardless of whether the stoma was created by surgery or other means. The term "user" may refer to an ostomate, or to another person assisting the ostomate, for example, with emptying of the stomal output from the cavity.

In this specification, the ostomy appliances disclosed herein may, for example, be used for managing a stoma created by an esophagostomy, a gastrostomy, a cholecystostomy, a choledochostomy, a cecostomy, a colostomy, a duodenostomy, an ileostomy, a jejunostomy, an appendicostomy, a tracheostomy, a urostomy, a nephrostomy, an ureterostomy, or a vesicostomy. The ostomy appliances disclosed herein may be used with additional devices including, but not limited to, a shunt, a catheter, a plug or a fecal management system.

In this specification locations and orientations of features may be described with reference to the ostomy appliance being "in use", "orientated as it would be in use" or similar. Such terms refer to the intended orientation of the ostomy appliance when it is adhered to a body of an ostomate with the ostomate in a standing position, irrespective of whether the ostomy appliance is currently performing such a use or the actual position of the ostomate. The terms "upper", "lower", "top", "bottom" and related terms refer to the relative position of a part or portion of the ostomy appliance when orientated as it would be in use. For example, an apex of the ostomy appliance may be referred to as an "upper" apex in use of the ostomy appliance. In such an example, said apex will be intended to be the uppermost apex (in the vertical direction) of the ostomy appliance when attached to the body of a standing ostomate. However the reader skilled in the art will appreciate that before attachment to the ostomate said apex may not always be the uppermost apex and in addition when attached the apex may not always be the uppermost apex if the ostomate adopts a non-standing position, for example lying down.

In this specification the terms "inner" and "outer" refer to the relative position of a part or portion of the ostomy appliance with reference to the body of an ostomate when the ostomy appliance is attached to the body. "Inner" refers to a position relatively closer to the body of the ostomate than a comparative position that is "outer". "Outer" refers to a position relatively further away from the body of the ostomate than a comparative position that is "inner". In this specification the term "peripheral" refers to a portion situated on or towards an edge of the item being referred to.

The present disclosure provides an ostomy appliance comprising: at least one appliance wall of flexible sheet material forming a cavity for containing a stomal output comprising stomal gas and stomal liquid and/or solids, the at least one appliance wall comprising a stomal inlet for receiving the stomal output and a gas vent for allowing the stomal gas to migrate out of the cavity; and a filter arrangement mounted to the at least one appliance wall and comprising at least one filter channel extending from at least one filter channel inlet to a filter channel outlet, wherein the at least one filter channel inlet is located in the cavity for receiving the stomal output from the cavity and the filter channel outlet is mounted in communication with the gas vent for allowing stomal gas to migrate out of the at least one filter channel to the gas vent.

The present disclosure also provides a method of manufacturing an ostomy appliance comprising: forming at least one appliance wall from flexible sheet material comprising a stomal inlet and a gas vent; forming a filter arrangement comprising at least one filter channel extending from at least one filter channel inlet to a filter channel outlet; and mounting the filter arrangement and at least one appliance wall to one another such that: the at least one appliance wall forms a cavity for containing a stomal output comprising stomal gas and stomal liquid and/or solids, the stomal inlet being arranged to receiving the stomal output and the gas vent being arranged to allow the stomal gas to migrate out of the cavity; and the at least one filter channel inlet is located in the cavity and is arranged to receive the stomal output from the cavity and the filter channel outlet is mounted in communication with the gas vent to allow stomal gas to migrate out of the at least one filter channel to the gas vent.

In use stomal output may be received in the cavity through the stomal inlet. Stomal gas may migrate from the cavity to the at least one filter channel inlet, through the at least one filter channel and out of the ostomy appliance via the at least one filter channel outlet and gas vent. The gas vent may therefore allow the stomal gas accumulating in the ostomy appliance to migrate therefrom and prevent it from bulging outwards.

However, as the ostomate moves around with the ostomy appliance attached they may change the orientation of the ostomy appliance such that the stomal solids and/or liquid contacts the at least one filter channel inlet (e.g. if the ostomy appliance is upside down or on its side when the ostomate is lying down). Under such conditions, some stomal solids and/or liquid may enter the at least one filter channel via the at least one filter channel inlet.

The filter arrangement may comprise first and second filter walls of flexible sheet material forming the at least one filter channel. The at least one filter channel extends between the first and second filter walls around at least one bend for restricting the passage of stomal liquid and/or solids along the at least one filter channel.

The at least one bend may restrict and/or filter the flow of stomal solids and/or liquid from reaching the filter channel outlet and prevent them from contacting the gas vent. In particular, the at least one bend may create at least one pinch point and when stomal output reaches the at least one bend it may become blocked with the stomal output. When the stomal gas builds up at the at least one bend due to it forming the at least one pinch point the pressure may force the first and second filter walls apart at the at least one pinch point. As a result, the stomal gas may be able to flow around the at least one bend, which thus acts as a self-regulating valve, whilst the stomal solids and/or liquid may not be able to pass beyond the at least one bend. The gas vent may thus be kept clear of stomal liquid and/or solids and it may not become clogged such that it can still effectively vent stomal gas.

The at least one filter channel may extend along at least one channel section extending to and/or from the at least one bend. In the at least one channel section the first and second walls may be substantially parallel to the at least one appliance wall. The filter channel may be turned back upon itself about the at least one bend. The method of forming the filter arrangement may therefore comprise folding the at least one filter channel back upon itself at least once to form the at least one bend. Such arrangements may beneficially form effective pinch points to assist in restricting the flow of stomal solids and/or liquid along the filter channel.

The at least one filter channel may extend between the first and second filter walls around first and second bends such that the at least one filter channel is Z-shaped. The use of multiple bends may assist in providing further restrictions to the passage of the stomal liquids and/or solids.

The at least one filter channel inlet and/or outlet may be located, in use, above the centre of the stomal inlet. The first bend may be located above the second bend and/or filter channel inlet and the second bend may be located below the filter channel outlet. As a result, gravity may assist in holding some of the stomal liquids and/or solids from travelling from the second bend towards the filter channel outlet.

The at least one bend may comprise a first bend and the at least one filter channel may comprise a first channel section extending to the first bend and a second channel section extending from the first bend. The first channel section may extend from the at least one filter channel inlet to the first bend. The at least one bend may comprise a second bend and the at least one filter channel may extend along the second channel section from the first bend to the second bend and may comprise a third channel section extending from the second bend. The third channel section may extend from the second bend to the filter channel outlet.

The first or second filter wall may form the inside of the at least one bend and may be formed from at least one flexible sheet overlapped upon itself around the at least one bend or may be formed from a flexible sheet extending from the inside of and away from the at least one bend. The first or second filter wall may form the outside of the at least one bend and may be formed from at least one flexible sheet overlapped upon itself around the at least one bend.

The first and second channel sections may extend between channel section ends and between channel section edges. The at least one filter channel inlet may be at a channel section end of the first channel section. The at least one bend may be between channel section ends of the first and second channel sections or the at least one bend may be between channel section edges of the first and second channel sections. The at least one filter channel may comprise first and second channel sections extending along a single axis in series prior to folding. The at least one filter channel may be folded back upon itself at least once to form the at least one bend between channel section ends of the first and second channel sections. Accordingly, in one embodiment there is provided a method of manufacturing an ostomy appliance comprising: forming at least one appliance wall from flexible sheet material comprising a stomal inlet and a gas vent; forming a filter arrangement comprising first and second filter walls of flexible sheet material forming at least one filter channel extending from at least one filter channel inlet to a filter channel outlet, wherein the at least one filter channel extends between the first and second filter walls around at least one bend; and mounting the filter arrangement and at least one appliance wall to one another such that: the at least one appliance wall forms a cavity for containing a stomal output comprising stomal gas and stomal liquid and/or solids, the stomal inlet being arranged to receiving the stomal output and the gas vent being arranged to allow the stomal gas to migrate out of the cavity; the at least one filter channel inlet is located in the cavity and is arranged to receive the stomal output from the cavity and the filter channel outlet is mounted in communication with the gas vent to allow stomal gas to migrate out of the at least one filter channel to the gas vent; and the at least one bend is arranged to restrict the passage of stomal liquid and/or solids along the at least one filter channel, wherein the at least one filter channel comprises first and second channel sections extending along a single axis in series prior to folding and wherein the at least one filter channel is folded back upon itself at least once to form the at least one bend between channel section ends of the first and second channel sections.

The at least one filter channel may comprise first and second channel sections extending parallel to one another prior to folding. The at least one filter channel may be folded back upon itself at least once to form the at least one bend between channel section edges of the first and second channel sections. Accordingly, in one embodiment, there is provided a method of manufacturing an ostomy appliance comprising: forming at least one appliance wall from flexible sheet material comprising a stomal inlet and a gas vent; forming a filter arrangement comprising first and second filter walls of flexible sheet material forming at least one filter channel extending from at least one filter channel inlet to a filter channel outlet, wherein the at least one filter channel extends between the first and second filter walls around at least one bend; and mounting the filter arrangement and at least one appliance wall to one another such that: the at least one appliance wall forms a cavity for containing a stomal output comprising stomal gas and stomal liquid and/or solids, the stomal inlet being arranged to receiving the stomal output and the gas vent being arranged to allow the stomal gas to migrate out of the cavity; the at least one filter channel inlet is located in the cavity and is arranged to receive the stomal output from the cavity and the filter channel outlet is mounted in communication with the gas vent to allow stomal gas to migrate out of the at least one filter channel to the gas vent; and the at least one bend is arranged to restrict the passage of stomal liquid and/or solids along the at least one filter channel, wherein the at least one filter channel comprises first and second channel sections extending parallel to one another prior to folding and wherein the at least one filter channel is folded back upon itself at least once to form the at least one bend between channel section edges of the first and second channel sections.

The ostomy appliance may further comprise at least one gas filter element located adjacent to the gas vent. The at least one gas filter element may be located in the at least one filter channel adjacent to the filter channel outlet. The gas vent may be located, in use, in the upper half of the ostomy appliance and may comprise at least one aperture in the at least one appliance wall.

The at least one appliance wall may comprise inner and outer walls. The inner and outer walls may be joined together, preferably around a peripheral joint. The filter arrangement may be located between the inner and outer walls and may be attached to the inner and/or outer walls, such as at least partially by the peripheral joint.

The filter arrangement may comprise first and second filter channels extending from first and second filter channel inlets respectively to the filter channel outlet. Each of the first and second filter channels may extend between the first and second filter walls around at least one bend for restricting the passage of stomal liquid and/or solids along the first and second filter channels. By having multiple filter channels the gas flow rate to the filter channel outlet may be increased and thus bulging further reduced. The first and second filter channels may extend substantially perpendicular to one another from the gas vent.

Accordingly in one embodiment, there is provided an ostomy appliance comprising: at least one appliance wall of flexible sheet material forming a cavity for containing a stomal output comprising stomal gas and stomal liquid and/or solids, the at least one appliance wall comprising a stomal inlet for receiving the stomal output and a gas vent for allowing the stomal gas to migrate out of the cavity; and a filter arrangement mounted to the at least one appliance wall and comprising first and second filter walls of flexible sheet material forming at least one filter channel extending from at least one filter channel inlet to a filter channel outlet, wherein the at least one filter channel inlet is located in the cavity for receiving the stomal output from the cavity and the filter channel outlet is mounted in communication with the gas vent for allowing stomal gas to migrate out of the at least one filter channel to the gas vent, wherein the at least one filter channel extends between the first and second filter walls around at least one bend for restricting the passage of stomal liquid and/or solids along the at least one filter channel, wherein the ostomy appliance further comprises first and second filter channels extending from first and second filter channel inlets respectively to the filter channel outlet, wherein: each of the first and second filter channels extend between the first and second filter walls around at least one bend for restricting the passage of stomal liquid and/or solids along the first and second filter channels; and the first and second filter channels extend substantially perpendicular to one another from the gas vent.

The filter arrangement may comprise at least one separation element extending at least partially along the at least one filter channel for maintaining the at least one filter channel in an open configuration along at least part of the at least one filter channel for allowing stomal gas to pass therethough. In particular, the at least one separation element may extend at least partially along the at least one filter channel for separating the first and second filter walls from one another along at least part of the at least one filter channel. The separation element may extend around at least one bend. The separation element therefore prevents the first and second filter walls from sticking to one another and the filter channel from sticking to itself and forming a restriction in the at least one filter channel.

The separation element may comprise a mesh. A mesh may be particularly suitable because it may provide a sufficiently complex path to block the passage of stomal liquids and solids, but the at least one mesh channel may allow the flow of stomal gas. The mesh may be rigid. The mesh may comprise a regular array of wefts and warps. The at least one separation element may comprise at least one separation element channel and/or the mesh may comprise at least one mesh channel extending therealong, for allowing stomal gas to pass through the at least one separation element or mesh to the filter channel outlet. The at least one separation channel may be formed between adjacent warps or adjacent wefts of the at least one mesh. As a result, the at least one separation element channel may ensure that there is always a gas pathway to the filter channel outlet. Accordingly, in one embodiment, there is provided an ostomy appliance comprising: at least one appliance wall of flexible sheet material forming a cavity for containing a stomal output comprising stomal gas and stomal liquid and/or solids, the at least one appliance wall comprising a stomal inlet for receiving the stomal output and a gas vent for allowing the stomal gas to migrate out of the cavity; and a filter arrangement mounted to the at least one appliance wall and comprising: at least one filter channel extending from at least one filter channel inlet to a filter channel outlet, wherein the at least one filter channel inlet is located in the cavity for receiving the stomal output from the cavity and the filter channel outlet is mounted in communication with the gas vent for allowing stomal gas to migrate out of the at least one filter channel to the gas vent; and at least one separation element extending at least partially along the at least one filter channel for maintaining the at least one filter channel in an open configuration along at least part of the at least one filter channel for allowing stomal gas to pass therethough, wherein: the at least one separation element comprises at least one mesh; the at least one separation element comprises at least one separation element channel therealong for stomal gas to pass through the at least one separation element to the filter channel outlet; and, the at least one separation channel is formed between adjacent warps or adjacent wefts of the at least one mesh.

The filter arrangement may comprise the at least one separation element in combination with the aforementioned embodiment in which the filter arrangement comprises first and second filter walls of flexible sheet material forming the at least one filter channel and wherein the at least one filter channel extends between the first and second filter walls around at least one bend for restricting the passage of stomal liquid and/or solids along the at least one filter channel.

Alternatively, the filter arrangement may comprise filter walls overlying one another to form the at least one filter channel. Channel sections may be formed between the filter walls. The channel sections may be fluidly connected by at least one aperture through the filter walls.

The at least one separation element may comprise a hollow housing and at least one mesh located in and extending along at least part of the housing. The hollow housing may extend from at least one housing inlet to at least one housing outlet. The at least one housing outlet may be aligned with the filter channel outlet. The at least one housing inlet may be located adjacent to the at least one filter channel inlet. Accordingly, in one embodiment, there is provided an ostomy appliance comprising: at least one appliance wall of flexible sheet material forming a cavity for containing a stomal output comprising stomal gas and stomal liquid and/or solids, the at least one appliance wall comprising a stomal inlet for receiving the stomal output and a gas vent for allowing the stomal gas to migrate out of the cavity; and a filter arrangement mounted to the at least one appliance wall and comprising: at least one filter channel extending from at least one filter channel inlet to a filter channel outlet, wherein the at least one filter channel inlet is located in the cavity for receiving the stomal output from the cavity and the filter channel outlet is mounted in communication with the gas vent for allowing stomal gas to migrate out of the at least one filter channel to the gas vent; and at least one separation element extending at least partially along the at least one filter channel for maintaining the at least one filter channel in an open configuration along at least part of the at least one filter channel for allowing stomal gas to pass therethough, wherein the at least one separation element comprises a hollow housing and at least one mesh located in and extending along at least part of the housing, wherein the hollow housing extends from at least one housing inlet to at least one housing outlet, the at least one housing outlet being aligned with filter channel outlet.

The at least one filter channel may extend tortuously between a filter wall and the at least one appliance wall and may comprise a plurality of filter channel sections partially separated from each other by attachment lines between the filter wall and the at least one appliance wall.

The ostomy appliance may further comprise a shield wall extending partially between the inner and outer walls and arranged to overlap the stomal inlet. The shield wall may therefore deflect stomal output downwardly from the stomal inlet.

Accordingly, in one embodiment, there is provided an ostomy appliance comprising: at least one appliance wall of flexible sheet material forming a cavity for containing a stomal output comprising stomal gas and stomal liquid and/or solids, the at least one appliance wall comprising a stomal inlet for receiving the stomal output and a gas vent for allowing the stomal gas to migrate out of the cavity; and a filter arrangement mounted to the at least one appliance wall and comprising: at least one filter channel extending from at least one filter channel inlet to a filter channel outlet, wherein the at least one filter channel inlet is located in the cavity for receiving the stomal output from the cavity and the filter channel outlet is mounted in communication with the gas vent for allowing stomal gas to migrate out of the at least one filter channel to the gas vent; and at least one separation element extending at least partially along the at least one filter channel for maintaining the at least one filter channel in an open configuration along at least part of the at least one filter channel for allowing stomal gas to pass therethough, wherein the at least one appliance wall comprises inner and outer walls and further comprising a shield wall extending partially between the inner and outer walls and arranged to overlap the stomal inlet.

Furthermore, in an alternative embodiment of the invention, there is provided an ostomy appliance comprising: at least one appliance wall of flexible sheet material forming a cavity for containing a stomal output comprising stomal gas and stomal liquid and/or solids, the at least one appliance wall comprising a stomal inlet for receiving the stomal output and a gas vent for allowing the stomal gas to migrate out of the cavity; and a filter arrangement mounted to the at least one appliance wall and comprising first and second filter walls of flexible sheet material forming at least one filter channel extending from at least one filter channel inlet to a filter channel outlet, wherein the at least one filter channel inlet is located in the cavity for receiving the stomal output from the cavity and the filter channel outlet is mounted in communication with the gas vent for allowing stomal gas to migrate out of the at least one filter channel to the gas vent, wherein the at least one filter channel extends between the first and second filter walls around at least one bend for restricting the passage of stomal liquid and/or solids along the at least one filter channel, wherein the at least one appliance wall comprises inner and outer walls and further comprising a shield wall extending partially between the inner and outer walls and arranged to overlap the stomal inlet.

The shield wall may be attached to the inner and/or outer wall such that a gas path is formed between the shield wall and the at least one filter channel inlet. Accordingly in one embodiment of the invention, there is provided an ostomy appliance comprising: at least one appliance wall of flexible sheet material forming a cavity for containing a stomal output comprising stomal gas and stomal liquid and/or solids, the at least one appliance wall comprising a stomal inlet for receiving the stomal output and a gas vent for allowing the stomal gas to migrate out of the cavity; and a filter arrangement mounted to the at least one appliance wall and comprising first and second filter walls of flexible sheet material forming at least one filter channel extending from at least one filter channel inlet to a filter channel outlet, wherein the at least one filter channel inlet is located in the cavity for receiving the stomal output from the cavity and the filter channel outlet is mounted in communication with the gas vent for allowing stomal gas to migrate out of the at least one filter channel to the gas vent, wherein the at least one filter channel extends between the first and second filter walls around at least one bend for restricting the passage of stomal liquid and/or solids along the at least one filter channel, wherein: the at least one appliance wall comprises inner and outer walls and further comprising a shield wall extending partially between the inner and outer walls and arranged to overlap the stomal inlet; and the shield wall is attached to the inner and/or outer wall such that a gas path is formed between the shield wall and the at least one filter channel inlet.

The present disclosure therefore provides an ostomy appliance comprising: inner and outer walls of flexible sheet material forming a cavity for containing a stomal output, the inner wall comprising a stomal inlet for receiving the stomal output; and a shield wall of flexible sheet material extending between the inner and outer walls across the stomal inlet and comprising a spacer arrangement for at least partially separating the shield wall from the inner and/or outer wall for forming a fluid path therebetween, the spacer arrangement comprising at least one undulation of the flexible sheet material of the shield wall.

The present disclosure further provides a method of manufacturing an ostomy appliance comprising: attaching inner and outer walls of flexible sheet material together to form a cavity for containing a stomal output, the inner wall comprising a stomal inlet for receiving the stomal output; attaching a shield wall of flexible sheet material to the inner and/or outer wall such that the shield wall extends across the stomal inlet; and forming at least one undulation in the flexible sheet material of the shield wall to form a spacer arrangement for at least partially separating the shield wall from the inner and/or outer wall for forming a fluid path therebetween.

In such arrangements the outer wall may comprise a gas vent for allowing stomal gas of the stomal output to migrate out of the cavity and wherein the fluid path allows stomal gas to reach the gas vent. The ostomy appliance may further comprise a filter arrangement mounted over the gas vent for allowing stomal gas to migrate from the cavity, through the filter arrangement and out of the ostomy appliance via the gas vent. The filter arrangement may be as disclosed herein. The at least one undulation may form a fluid path extending adjacent to the shield wall to the at least one filter channel inlet. The shield wall may be attached and located between the filter arrangement and the inner wall.

The maintenance of the fluid path may ensure that stomal gas can effectively flow through the stomal inlet and between the shield wall and the inner wall, as well as between the shield wall and outer wall up to the filter channel inlet. The shield wall may therefore prevent stomal output from passing through the stomal inlet and directly contacting any filter arrangement.

The shield wall may comprise flexible sheet material extending across a shield wall area. The shield wall may overlap the inner and/or outer wall across an overlap area of the inner and/or outer wall. The shield wall area may be greater than the overlap area. Thus the at least one undulation may be formed by a region of excess flexible sheet material of the shield wall relative to the overlapping region of the inner and/or outer wall. As a result, the spacer arrangement can be formed from only the flexible sheet material. The thickness of the flexible sheet material of the shield wall may be constant across the at least one undulation.

The shield wall may extend from a top of the ostomy appliance between edges of the ostomy appliance. The shield wall may extend to a lower edge separated from a cavity lower end such that stomal output can pass between the lower edge and cavity lower end. The shield wall may extend from a top of the ostomy appliance between edges of the ostomy appliance and may extend to a lower edge separated from a cavity lower end such that stomal output can pass between the lower edge and cavity lower end. The shield wall may comprise a substantially impermeable region opposite and entirely overlapping the stomal inlet.

The shield wall may comprise at least one shield wall aperture therethrough, the at least one shield wall aperture being located adjacent to and not overlapping the stomal inlet. The at least one shield wall aperture may assist in preventing additional and unnecessary wrinkles forming in the shield wall that might otherwise hinder the flow of stomal gas.

The flexible sheet material of the shield wall may extend across a substantially flat plane prior to forming the at least one undulation. Forming the at least one undulation may comprise bringing at least part of the flexible sheet material of the shield wall out of the flat plane. Forming the at least one undulation may occur during the attaching of the shield wall to the inner and/or outer wall. Accordingly, in one embodiment there is provided a method of manufacturing an ostomy appliance comprising: attaching inner and outer walls of flexible sheet material together to form a cavity for containing a stomal output, the inner wall comprising a stomal inlet for receiving the stomal output; attaching a shield wall of flexible sheet material to the inner and/or outer wall such that the shield wall extends across the stomal inlet; and forming at least one undulation in the flexible sheet material of the shield wall to form a spacer arrangement for at least partially separating the shield wall from the inner and/or outer wall for forming a fluid path therebetween, wherein the method further comprises forming the at least one undulation during the attaching of the shield wall to the inner and/or outer wall.

The method may comprise locating the shield wall over the inner or outer wall. The method may comprise moving at least part of the shield wall relative to the inner or outer wall to form the at least one undulation. The method may comprise attaching the shield wall to the inner and/or outer wall to maintain the at least one undulation in the shield wall. Accordingly in one embodiment, there is provided a method of manufacturing an ostomy appliance comprising: attaching inner and outer walls of flexible sheet material together to form a cavity for containing a stomal output, the inner wall comprising a stomal inlet for receiving the stomal output; attaching a shield wall of flexible sheet material to the inner and/or outer wall such that the shield wall extends across the stomal inlet; and forming at least one undulation in the flexible sheet material of the shield wall to form a spacer arrangement for at least partially separating the shield wall from the inner and/or outer wall for forming a fluid path therebetween, wherein the method further comprises locating the shield wall over the inner or outer wall, moving at least part of the shield wall relative to the inner or outer wall to form the at least one undulation and attaching the shield wall to the inner and/or outer wall to maintain the at least one undulation in the shield wall.

After locating the shield wall over the inner or outer wall, the shield wall may be partially attached to the inner or outer wall. Accordingly, in one embodiment, there is provided a method of manufacturing an ostomy appliance comprising: attaching inner and outer walls of flexible sheet material together to form a cavity for containing a stomal output, the inner wall comprising a stomal inlet for receiving the stomal output; attaching a shield wall of flexible sheet material to the inner and/or outer wall such that the shield wall extends across the stomal inlet; and forming at least one undulation in the flexible sheet material of the shield wall to form a spacer arrangement for at least partially separating the shield wall from the inner and/or outer wall for forming a fluid path therebetween, wherein the method further comprises locating the shield wall over the inner or outer wall, moving at least part of the shield wall relative to the inner or outer wall to form the at least one undulation and attaching the shield wall to the inner and/or outer wall to maintain the at least one undulation in the shield wall, and wherein after locating the shield wall over the inner or outer wall the shield wall is partially attached to the inner or outer wall.

The ostomy appliance may be a closed appliance or an open appliance. A closed appliance is not configured for stomal output to be drained from the cavity. Thus, a closed appliance may typically be configured as a one-use, disposable and non-reusable appliance. In the ostomy appliance of the present disclosure the cavity may therefore be entirely sealed within the ostomy appliance from the external environment other than via the gas vent and the stomal inlet. An open appliance is configured for stomal output to be drained from the cavity. Thus, an open appliance may be configured as a reusable appliance, such that it can be reused and emptied multiple times whilst attached to the body, although this is not essential. In an open appliance the stomal output may be drained intermittently as instigated by an action of the ostomate or may be drained intermittently or continuously due to the cavity being fluidly connected to a drain. The ostomy appliance of the present disclosure may therefore comprise a selectively openable drain for allowing the stomal output to be selectively drained from the cavity.

Accordingly, in one embodiment, there is provided an ostomy appliance comprising: at least one appliance wall of flexible sheet material forming a cavity for containing a stomal output comprising stomal gas and stomal liquid and/or solids, the at least one appliance wall comprising a stomal inlet for receiving the stomal output and a gas vent for allowing the stomal gas to migrate out of the cavity; and a filter arrangement mounted to the at least one appliance wall and comprising: at least one filter channel extending from at least one filter channel inlet to a filter channel outlet, wherein the at least one filter channel inlet is located in the cavity for receiving the stomal output from the cavity and the filter channel outlet is mounted in communication with the gas vent for allowing stomal gas to migrate out of the at least one filter channel to the gas vent; and at least one separation element extending at least partially along the at least one filter channel for maintaining the at least one filter channel in an open configuration along at least part of the at least one filter channel for allowing stomal gas to pass therethough, wherein the ostomy appliance further comprises a selectively openable drain for allowing the stomal output to be selectively drained from the cavity or wherein the cavity is sealed within the ostomy appliance other than via the gas vent and the stomal inlet.

Furthermore, in an alternative embodiment, there is provided an ostomy appliance comprising: at least one appliance wall of flexible sheet material forming a cavity for containing a stomal output comprising stomal gas and stomal liquid and/or solids, the at least one appliance wall comprising a stomal inlet for receiving the stomal output and a gas vent for allowing the stomal gas to migrate out of the cavity; and a filter arrangement mounted to the at least one appliance wall and comprising first and second filter walls of flexible sheet material forming at least one filter channel extending from at least one filter channel inlet to a filter channel outlet, wherein the at least one filter channel inlet is located in the cavity for receiving the stomal output from the cavity and the filter channel outlet is mounted in communication with the gas vent for allowing stomal gas to migrate out of the at least one filter channel to the gas vent, wherein the at least one filter channel extends between the first and second filter walls around at least one bend for restricting the passage of stomal liquid and/or solids along the at least one filter channel, wherein the ostomy appliance further comprises a selectively openable drain for allowing the stomal output to be selectively drained from the cavity or wherein the cavity is sealed within the ostomy appliance other than via the gas vent and the stomal inlet.

The ostomy appliance may comprise a wafer for attaching it the body of an ostomate. The ostomy wafer may have an opening for the stoma, which may be cut to a required size by a user before attachment. The ostomy wafer may comprises at least one adhesive layer on a body-facing side for adhering the ostomy wafer to the body of the ostomate. A release liner may cover a body-facing side of the ostomy wafer that is removed by the user prior to fitting to the skin. The term "wafer" may be used interchangeably with the terms "adapter", "baseplate", or "layered adhesive wafer."

The ostomy appliance may be a one-piece appliance and may comprise a wafer non-releasably attached to the inner wall around the stomal inlet such that the ostomy wafer cannot easily be separated without risk of damaging the appliance. The ostomy appliance may be a two-piece appliance and may comprise a releasable coupling attached to the inner wall around the stomal inlet and a wafer attached to the releasable coupling such that the coupling can be disengaged to separate the wafer from the rest of the ostomy appliance. The ostomy wafer and/or releasable coupling may be located at least partially in an upper peripheral region of the ostomy appliance.

Accordingly, in one embodiment, there is provided an ostomy appliance comprising: at least one appliance wall of flexible sheet material forming a cavity for containing a stomal output comprising stomal gas and stomal liquid and/or solids, the at least one appliance wall comprising a stomal inlet for receiving the stomal output and a gas vent for allowing the stomal gas to migrate out of the cavity; and a filter arrangement mounted to the at least one appliance wall and comprising: at least one filter channel extending from at least one filter channel inlet to a filter channel outlet, wherein the at least one filter channel inlet is located in the cavity for receiving the stomal output from the cavity and the filter channel outlet is mounted in communication with the gas vent for allowing stomal gas to migrate out of the at least one filter channel to the gas vent; and at least one separation element extending at least partially along the at least one filter channel for maintaining the at least one filter channel in an open configuration along at least part of the at least one filter channel for allowing stomal gas to pass therethough, wherein the ostomy appliance further comprises a wafer non-releasably attached to the at least one appliance wall around the stomal inlet or a releasable coupling attached to the at least one appliance wall around the stomal inlet and a wafer attached to the releasable coupling.

Furthermore, in an alternative embodiment, there is provided an ostomy appliance comprising: at least one appliance wall of flexible sheet material forming a cavity for containing a stomal output comprising stomal gas and stomal liquid and/or solids, the at least one appliance wall comprising a stomal inlet for receiving the stomal output and a gas vent for allowing the stomal gas to migrate out of the cavity; and a filter arrangement mounted to the at least one appliance wall and comprising first and second filter walls of flexible sheet material forming at least one filter channel extending from at least one filter channel inlet to a filter channel outlet, wherein the at least one filter channel inlet is located in the cavity for receiving the stomal output from the cavity and the filter channel outlet is mounted in communication with the gas vent for allowing stomal gas to migrate out of the at least one filter channel to the gas vent, wherein the at least one filter channel extends between the first and second filter walls around at least one bend for restricting the passage of stomal liquid and/or solids along the at least one filter channel, wherein the ostomy appliance further comprises a wafer non-releasably attached to the at least one appliance wall around the stomal inlet or a releasable coupling attached to the at least one appliance wall around the stomal inlet and a wafer attached to the releasable coupling.

The at least one appliance wall, inner wall, outer wall, first filter wall, second filter wall and/or shield wall may be formed from the same or different flexible sheet material and may be formed from at least one layer of such flexible sheet material. The flexible sheet(s) may comprise polyurethane, polyethylene (PE), polyvinylidene chloride (PVDC) and/or ethylene-vinyl acetate (EVA). The flexible sheet(s) may have a thickness of about 50 to about 150 micrometres, preferably about 75 to about 100 micrometres. The flexible sheet(s) may comprise a single layer or a laminate of a plurality of layers.

BRIEF DESCRIPTION OF THE DRAWINGS

One or more embodiments of the disclosure will now be described, by way of example only, with reference to the accompanying drawings in which.

DETAILED DESCRIPTION OF THE DISCLOSURE

Figure 1:
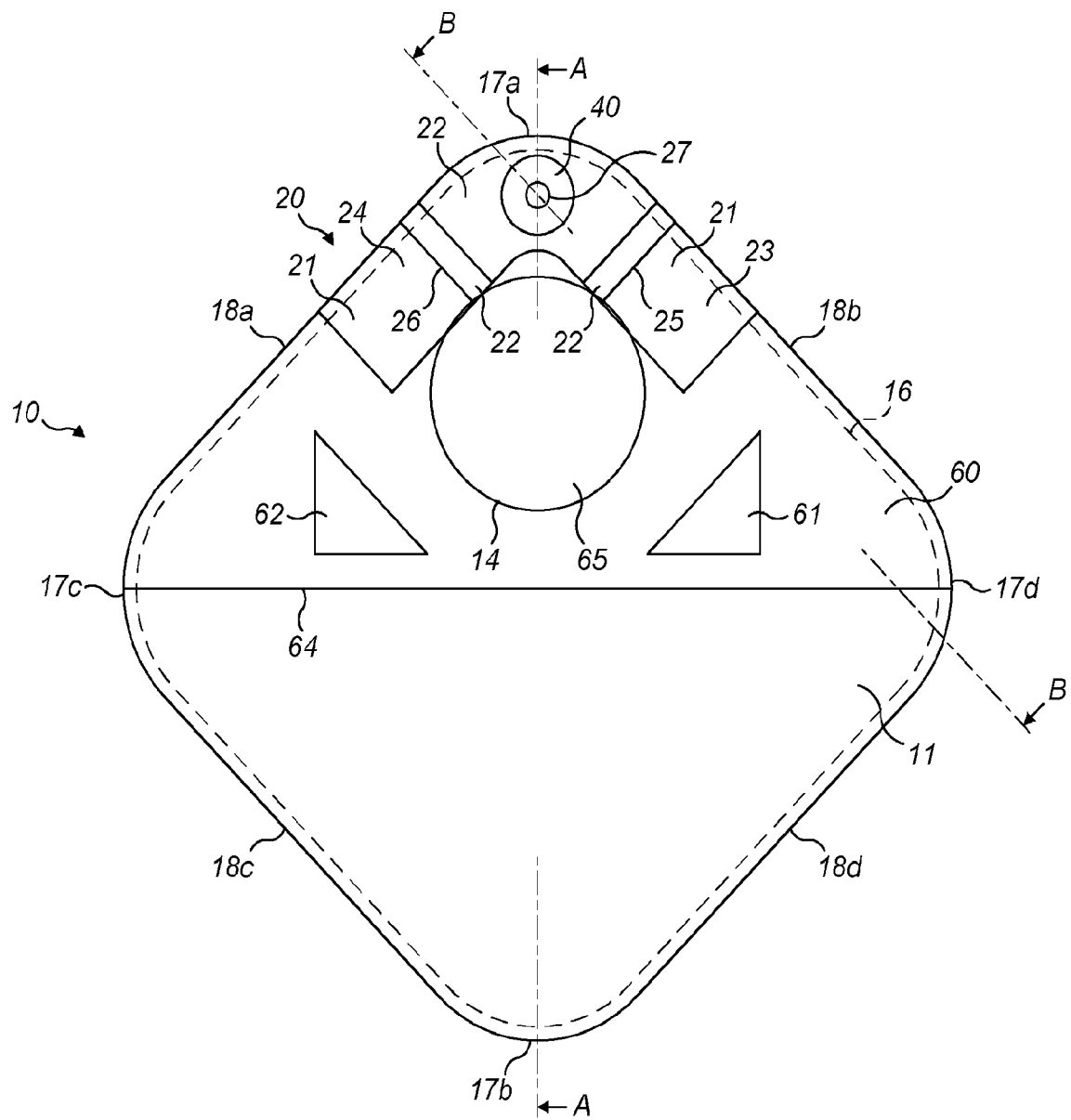
FIG. 1 is a front view of an embodiment of an ostomy appliance in accordance with the present disclosure.

In the following description, the equivalent reference numerals are used in different embodiments to denote equivalent or similar features. Unless defined otherwise, all technical and scientific terms used in this specification have the same meaning as is commonly understood by the reader skilled in the art to which the claimed subject matter belongs. It is to be understood that the foregoing summary of the disclosure and the following examples are exemplary and explanatory only and are not restrictive of any subject matter claimed.

The following description is directed to embodiments of the disclosure. The description of the embodiments is not meant to include all the possible embodiments of the disclosure that are claimed in the appended claims. Many modifications, improvements and equivalents which are not explicitly recited in the following embodiments may fall within the scope of the appended claims. Features described as part of one embodiment may be combined with features of one or more other embodiments unless the context clearly requires otherwise.

It is to be understood that at least some of the figures and descriptions of the disclosure have been simplified to focus on elements that are relevant for a clear understanding of the disclosure, while eliminating, for purposes of clarity, other elements that the reader skilled in the art will appreciate may also be required. Because such elements are well known to the reader skilled in the art, and because they do not necessarily facilitate a better understanding of the disclosure, a description of such elements is not provided herein.

In this specification, the use of the singular includes the plural unless the context clearly dictates otherwise. In this application, the use of "or" means "and/or" unless stated otherwise.

As used herein, ranges and amounts can be expressed as "about" a particular value or range. About also includes the exact amount. For example, "about 5 mm" means "about 5 mm" and also "5 mm." Generally, the term "about" includes an amount that would be expected to be within experimental error. The term "about" includes values that are within 10% less to 10% greater of the value provided. For example, "about 50%" means "between 45% and 55%." Also, by way of example, "about 30" means "between 27 and 33."

FIGS. 1 to 4 illustrate an embodiment of an ostomy appliance 10 according to the present disclosure. The ostomy appliance 10 may comprise a wafer and/or a coupling (not illustrated) and may be a one-piece or a two-piece appliance.

The ostomy appliance 10 may comprise at least one appliance wall 11, 12 of flexible sheet material forming a cavity 13 for containing stomal output. The at least one appliance wall 11, 12 may form the outer surface of the ostomy appliance 10 and may comprise an inner wall 11 and an outer wall 12 as illustrated. The cavity 13 is illustrated as a single volume, but in alternative embodiments it may be sub-divided into two or more chambers by, for example, partitions, wall members, filter elements and the like.

Prior to first use and stomal output entering the cavity 13 the ostomy appliance 10 may have a substantially flat configuration. In the flat configuration the ostomy appliance 10 has a substantially flat planar shape and the inner and outer walls 11, 12, and any further partitions or components therebetween are substantially adjacent to one another.

The at least one appliance wall 11, 12, preferably the inner wall 11 as illustrated, may comprise a stomal inlet 14 for receiving stomal output from the stoma into the cavity 13. The stomal inlet 14 may be an aperture through the inner wall 11. The at least one appliance wall 11, 12, preferably the outer wall 12 as illustrated, may comprise a gas vent 15 for allowing the stomal gas to migrate out of the cavity 13. The gas vent 15 may comprise at least one aperture through the outer wall 12.

The stomal inlet 14 and gas vent 15 may be located, in use, in the upper half of the ostomy appliance 10. The centre of the gas vent 15 may be located, in use, above the centre of the stomal inlet 14. Preferably the entire perimeter of the gas vent 15 is located, in use, above the entire perimeter of the stomal inlet 14 as shown in FIG. 1. The term "above" is intended to mean that the gas vent 15 is located, in use, uppermost of the stomal inlet 14 along a line parallel to the inner and outer walls 11, 12 when in the flat configuration.

The diameter of the at least one aperture of the gas vent 15 may be less than the diameter of the stomal inlet 14. The diameter of the at least one aperture of the gas vent 15 may at least about 1 mm, may be up to about 10 mm and/or may be about 5 mm. The diameter of the stomal inlet 14 may be at least about 10 mm, may be up to about 60 mm and/or may be about 45 mm. The distance between the, in use, top of the ostomy appliance 10 and centre of the stomal inlet 14 may be at least about 40 mm, may be up to about 60 mm and/or may be about 49 mm or about 50 mm.

The at least one appliance wall 11, 12 may be joined together to define the cavity 13 therebetween. The inner wall 11 and outer wall 12 may be joined together around their peripheral edges by use of welding, adhesive or equivalent means such that a peripheral joint 16 may extend around a full perimeter of the inner and outer walls 11, 12 to create a fluid-tight seal there between. The peripheral joint 16 may have a width of 1 to 3 mm, preferably about 2 mm. In the illustrated embodiment the ostomy appliance 10 is a closed appliance such that the cavity 13 is sealed within the ostomy appliance 10 other than via the stomal inlet 14 and gas vent 15. In alternative embodiments it may be an open appliance and may comprise a drain for allowing stomal output to flow out of the cavity 13.

The ostomy appliance 10, inner wall 11 and outer wall 12 may be substantially quadrilateral in shape as illustrated. In other embodiments they may have any other suitable shape, such as round or oval. The ostomy appliance 10, inner wall 11 and outer wall 12 may have a length of about 120 mm to about 200 mm, preferably about 140 mm to about 160 mm, for example about 145 mm, and may have a width of about 120 mm to about 200 mm, preferably about 140 mm to about 160 mm, for example about 140 mm or about 145 mm.

The inner wall 11 and the outer wall 12 may have one or more, preferably four, apexes 17*a-d*, at least one of which is preferably rounded as illustrated. The radius of curvature of each rounded apex 17*a-d* may be about 30 mm. When in use (i.e. when worn by an ostomate) the inner and outer walls 11, 12 may comprise an upper apex 17*a* which points substantially vertically upwards, a lower apex 17*b* which points substantially vertically downwards and opposed lateral apexes 17*c*, 17*d* which point substantially to each side, as shown by way of example in FIG. 1. The upper apex 17*a* may be joined to the opposed lateral apexes 17*c*, 17*d* by first and second edges 18*a*, 18*b* respectively. The lower apex 17*b* may be joined to the opposed lateral apexes 17*c*, 17*d* by third and fourth edges 18*c*, 18*d* respectively. One or more of the first, second, third and fourth edges 18*a-d* may be straight between their respective apexes 17*a-d*. Where the apex 17*a-d* is rounded, the edge 18*a-d* may be straight between the rounded apex(es) 17*a-d*.

The gas vent 15 may be located, in use, adjacent to the top of the ostomy appliance 10. As a result, the gas vent 15 may be located adjacent to the upper apex 17*a* between the first and second edges 18*a*, 18*b*.

The cavity 13 may extend between a cavity upper end 13*a* adjacent to the top of the ostomy appliance 10 and a cavity lower end 13*b* adjacent to the bottom of the ostomy appliance 10. Thus the cavity upper end 13*a* may be adjacent to the upper apex 17*a* and the cavity lower end 13*b* may be adjacent to the lower apex 17*b*. The gas vent 15 may be located adjacent to the cavity upper end 13*a*.

The ostomy appliance 10 may comprise a filter arrangement 20 for allowing stomal gas to exit the cavity 13 via the gas vent 15 and for filtering the passage of stomal solids and/or liquid so as to prevent them from exiting the cavity 13 via the gas vent 15. The filter arrangement 20 may be mounted to the at least one appliance wall 11, 12, may be mounted to at least the outer wall 12 and/or may be mounted between the inner and outer walls 11, 12. The filter arrangement 20 may be mounted over the gas vent 15.

Figure 2:
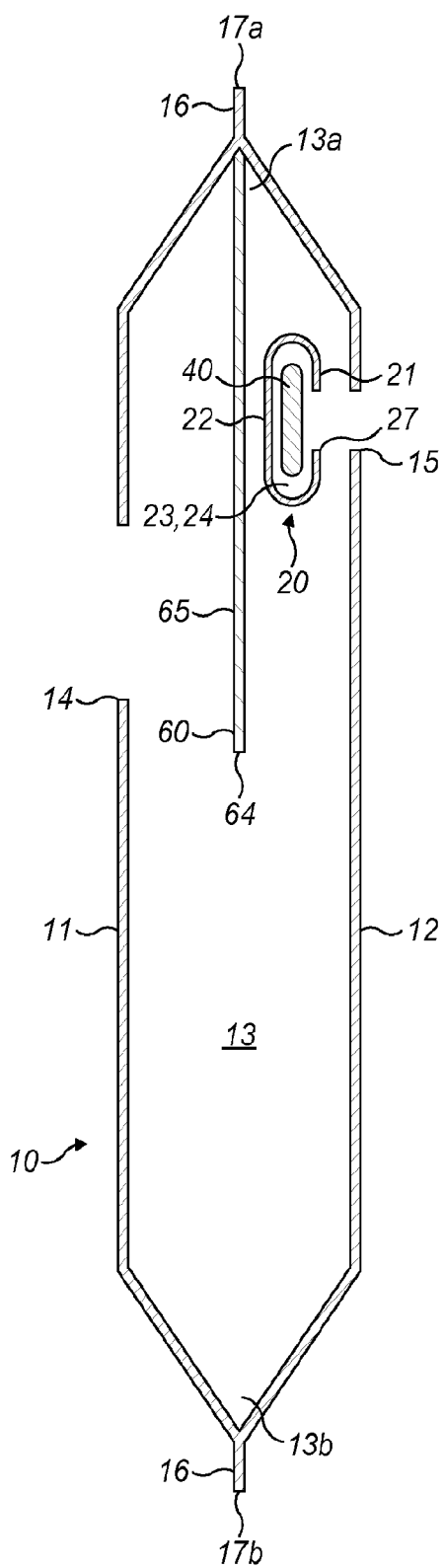
FIG. 2 is a cross-sectional view of the ostomy appliance of FIG. 1 through section A-A.
Figure 3:
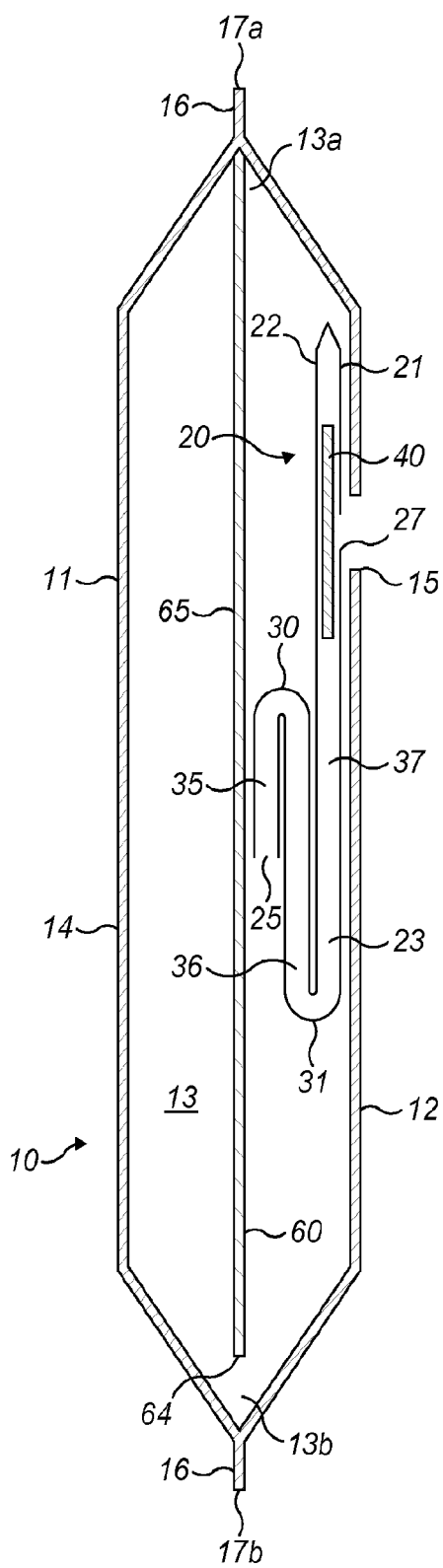
FIG. 3 is a cross-sectional view of the ostomy appliance of FIG. 1 through section B-B with a separation element of a filter arrangement hidden from view.
Figure 4:
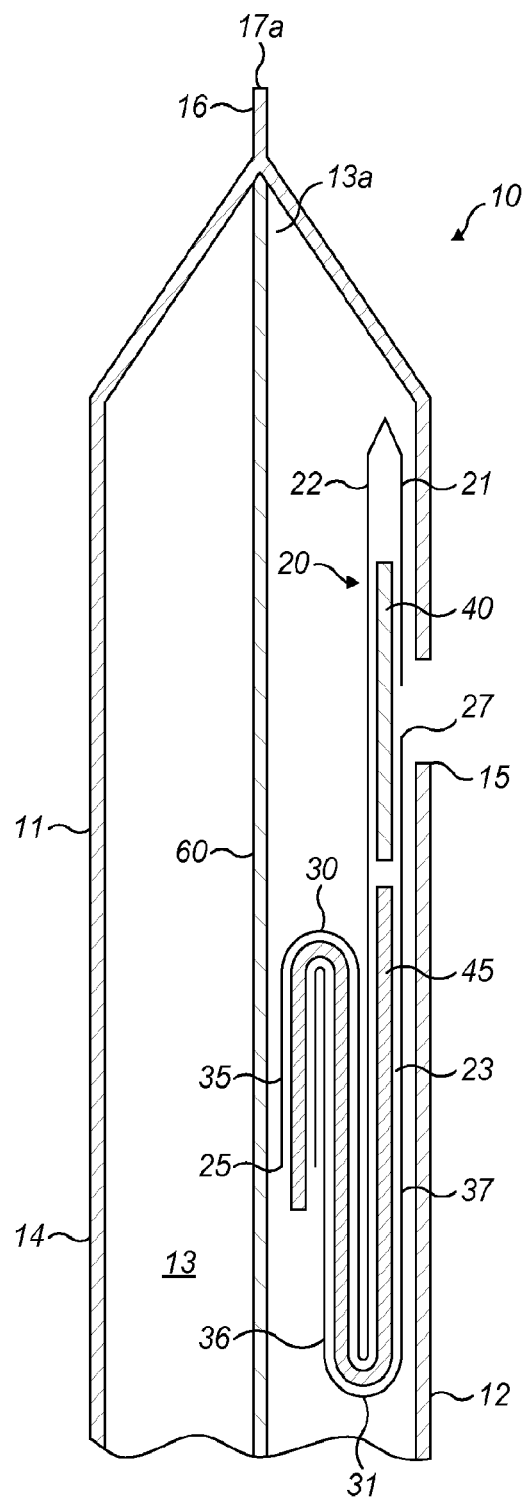
FIG. 4 is a partial cross-sectional view of the ostomy appliance of FIG. 1 through section B-B showing the separation element of the filter arrangement.

In FIGS. 2 to 4 the filter arrangement 20 is illustrated as being separated from the outer wall 12 for clarity, but may be in contact with and joined to the outer wall 12. The filter arrangement 20 may also extend into the peripheral joint 16 as illustrated in FIG. 1 and may be attached to the inner and outer walls 11, 12 by the peripheral joint 16 (this is not illustrated in FIGS. 2 to 4 for the sake of clarity). Thus the filter arrangement 20 may be located, in use, adjacent to the top of the ostomy appliance 10 and may extend along the edges of the inner and outer walls 11, 12. Thus the filter arrangement 20 may be located adjacent to the upper apex 17*a* between the first and second edges 18*a*, 18*b*.

Figure 5:
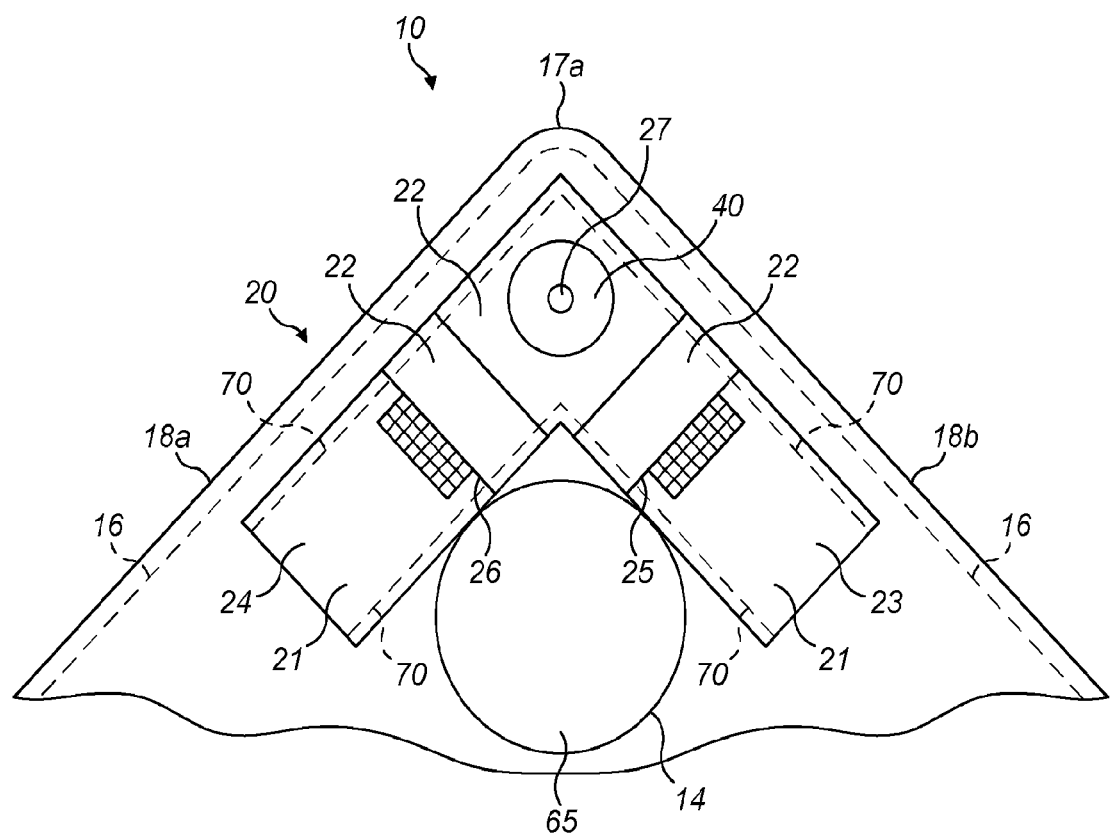
FIG. 5 is a partial front view of a further embodiment of an ostomy appliance in accordance with the present invention in which the filter arrangement is separated from a peripheral weld of the ostomy appliance.
Figure 6A:
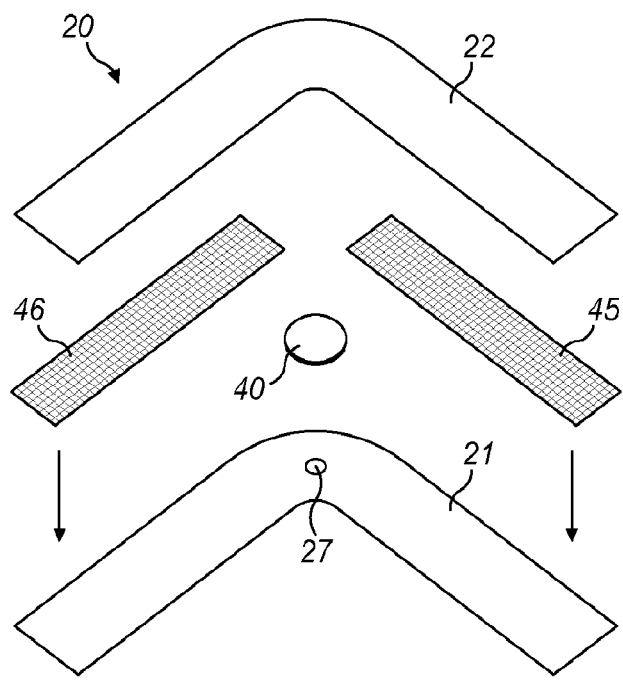
FIGS. 6A to 6F are perspective views illustrating the steps of forming the filter arrangements of FIGS. 1 to 5.
Figure 6B:
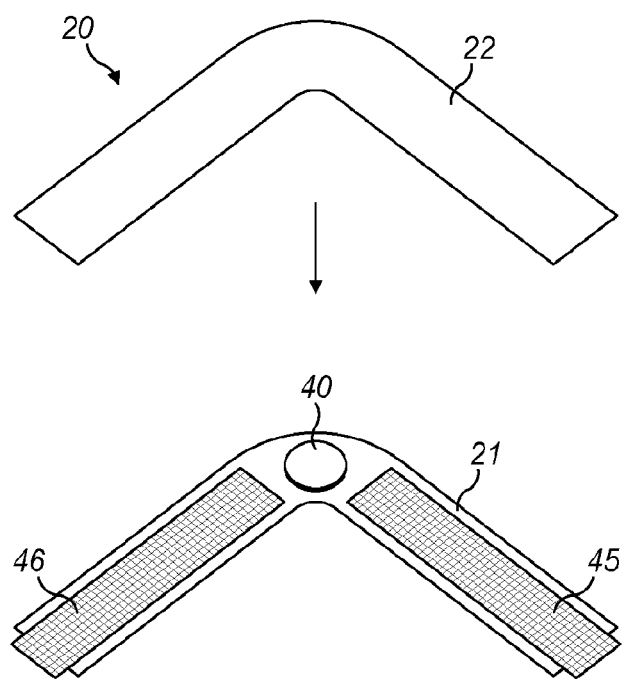
Figure 6C:
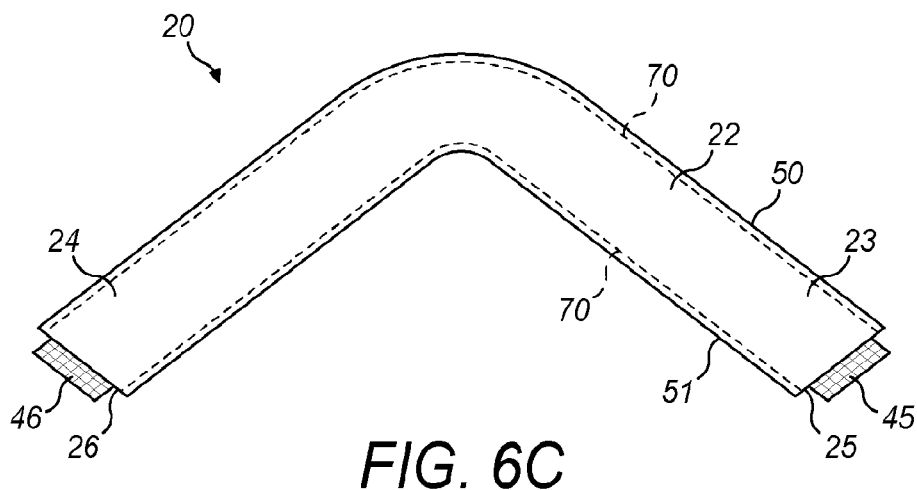
Figure 6D:
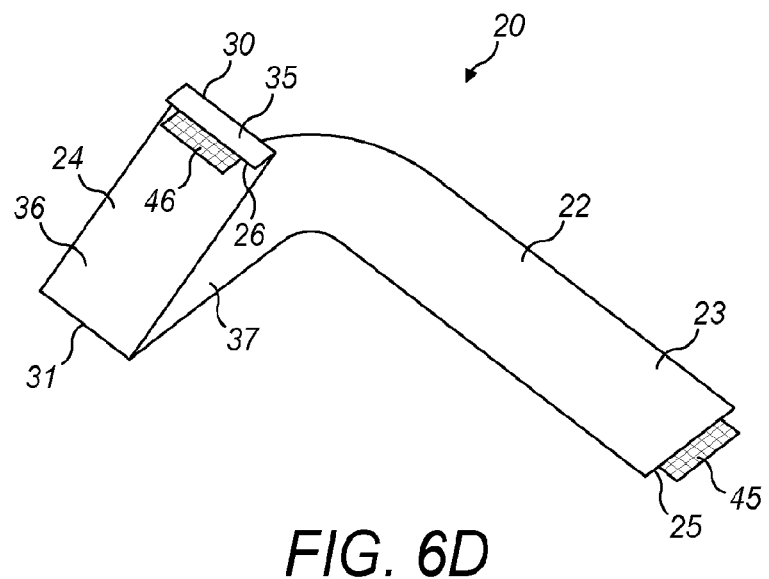
Figure 6E:
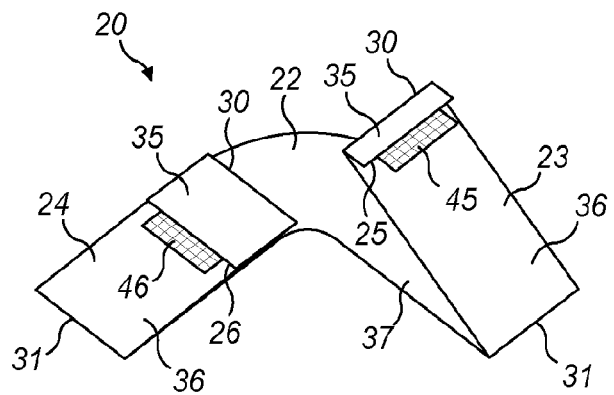
Figure 6F:
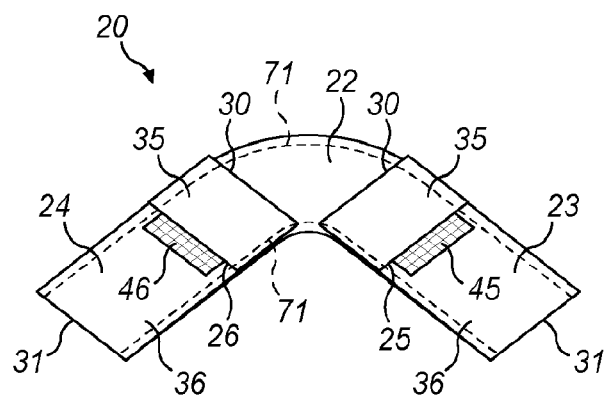

Alternatively, as shown in FIG. 5, the filter arrangement 20 may be separated from the peripheral joint 16 and thus may be separated from the edges, preferably first and second edges 18a, 18b. The filter arrangement 20 may be welded to the outer wall 12 separately to the peripheral joint 16 and may be welded adjacent to the peripheral joint 16. As a result, the thickness of the peripheral joint 16 may be reduced, thereby improving manufacturability and flexibility.

As best illustrated in FIGS. 3, 4 and 6A to 6F, the filter arrangement 20 may comprise first and second filter walls 21, 22 of flexible sheet material. The first and second filter walls 21, 22 may form at least one filter channel 23, 24 therebetween extending from at least one filter channel inlet 25, 26 to at least one filter channel outlet 27. In particular, the at least one filter channel 23, 24 may be formed between major planes of the flexible sheet material of the first and second filter walls 21, 22.

The first and second filter walls 21, 22 may comprise at least one strip of flexible sheet material joined together along at least one channel edge 50, 51, preferably first and second channel edges 50, 51, and the at least one filter channel 23, 24 may extend along the at least one channel edge 50, 51 between planes of the flexible sheet material. The first and second filter walls 21, 22 may each comprise a single continuous layer or strip of flexible sheet material forming the at least one filter channel 23, 24 as illustrated in FIGS. 3, 4 and 6A to 6F.

The at least one filter channel inlet 25, 26 may be for receiving the stomal output from the cavity 13 and thus may be located in the cavity 13. If the cavity 13 is divided into multiple chambers then the at least one filter channel inlet 25, 26 is preferably located in a chamber to which at least the stomal gas can migrate.

The at least one filter channel outlet 27 may be mounted in communication with the gas vent 15 and may be for allowing stomal gas to migrate out of the at least one filter channel 23, 24 to the gas vent 15. The filter channel outlet 27 may be located adjacent to and aligned with the gas vent 15 such that stomal gas passes from the filter channel outlet 27, through the gas vent 15 and out into the external environment around the ostomy appliance 10. The filter channel outlet 27 may be located through the first or second filter wall 21, 22 and may comprise an aperture therethrough as illustrated. The first or second filter wall 21, 22 comprising the filter channel outlet 27 may be mounted over and around the gas vent 15 such that the filter channel outlet 27 overlies the gas vent 15, for example by said first or second filter wall 21, 22 being joined to the outer wall 12.

As illustrated in FIGS. 1 and 6A to 6F, the at least one filter channel 23, 24 may comprise first and second filter channels 23, 24 extending from first and second filter channel inlets 25, 26 respectively to a filter channel outlet 27. The first and second filter channels 23, 24 may extend in different directions from the gas vent 15 and may extend substantially perpendicular to one another from the gas vent 15 as illustrated. As a result, the first and second filter channels 23, 24 may extend parallel to and along the first and second edges 18a, 18b from the gas vent 15.

The at least one filter channel 23, 24 may extend between the first and second filter walls 21, 22 around at least one bend 30 for restricting the passage of stomal liquid and/or solids along the at least one filter channel 23, 24. In particular, the first filter channel 23 may comprise at least one bend 30, and the second filter channel 24 may also comprise at least one bend 30, for restricting the passage of stomal liquid and/or solids along the first and/or second filter channels 23, 24.

The arrangement of the at least one bend 30 is illustrated in detail in FIGS. 3 and 4, which show at least one bend 30, 31 of the first filter channel 23. The following description is generally in reference to the first filter channel 23, but it will be appreciated that the at least one bend 30, 31, if any, of the second filter channel 24 may comprise the same features. The same reference numerals have been used in the drawings to denote the corresponding features of each of the first and second filter channels 23, 24.

The or each filter channel 23, 24 may be turned back upon itself about the at least one bend 30, 31. The or each filter channel 23, 24 (and the flow therealong) may extend into the at least one bend 30, 31 in a first direction and extend out of the at least one bend 30, 31 in an opposite second direction. Thus the or each filter channel 23, 24 may extend parallel to and between the inner and outer walls 11, 12, turn back upon itself about the at least one bend 30, 31 and then continue to extend parallel to and between the inner and outer walls 11, 12.

The or each filter channel 23, 24 may extend along at least one channel section 35, 36, 37 extending to and/or from the at least one bend 30, 31 and preferably between the first and second filter walls 21, 22. In the at least one channel section 35, 36, 37 the first and second filter walls 21, 22 are substantially parallel to the at least one appliance wall 11, 12, particularly the inner and outer walls 11, 12, when in a flat configuration.

The at least one channel section 35, 36, 37 may comprise a first channel section 35 extending to a first bend 30 and a second channel section 36 extending from the first bend 30. The first channel section 35 may extend from the respective filter channel inlet 25, 26 to the first bend 30. Although not illustrated, if the at least one bend 30, 31 comprises only the first bend 30 the second channel section 36 may extend from the first bend 30 to the filter channel outlet 27.

As in the illustrated embodiment the or each filter channel 23, 24 may extend between the first and second filter walls 21, 22 around first and second bends 30, 31 such that the or each filter channel 23, 24 is Z-shaped and/or has a tortuous path. The second channel section 36 therefore extends between the first and second bends 30, 31 and the at least one channel section 35, 36, 37 comprises a third channel section 37 extending between the second bend 31 and the filter channel outlet 27.

The first, second and, if present third, channel sections 35, 36, 37 may extend between channel section ends, may be elongate between the channel section ends and may extend between channel section edges 50, 51. In the embodiments of FIGS. 3, 4 and 6A to 6F, the at least one bend 30, 31 is between channel section ends. As a result, the fluid flow around the or each filter channel 23, 24 extends around about 180 degrees around a single axis around the at least one bend 30, 31. Thus the fluid flow only changes in direction about a single axis as it travels around the at least one bend 30, 31 between channel sections 35, 36, 37.

In particular, the first channel section 35 may extend between first channel section ends, the filter channel inlet 25, 26 being located at a first channel section end and the first bend 30 being located at the opposing first channel section end. The second channel section 36 may extend between second channel section ends, the first bend 30 being located at a second channel section end and the second bend 31 or filter channel outlet 27 being located at the opposing second channel section end. The third channel section 37 may extend between third channel section ends, the second bend 31 being located at a third channel section end and the filter channel outlet 27 being located at the opposing third channel section end.

The length along the or each filter channel 23, 24 from the respective filter channel inlet 25, 26 to the filter channel outlet 27 may be at least about 70 mm, may be up to about 120 mm and/or may be about 95 mm. The width of the or each filter channel 23, 24 may be at least about 15 mm, up to about 30 mm and/or may be about 22 mm. The first channel section 35 may be at least about 5 mm long, up to about 15 mm long and/or may be about 10 mm long. The second channel section 36 may be at least about 30 mm long, up to about 40 mm long and/or may be about 35 mm long. The third channel section 37 may be at least about 30 mm long, up to about 70 mm long and/or may be about 50 mm long.

Each of the inside and outside of each bend 30, 31 may be formed from one of the first and second filter walls 21, 22. As illustrated in FIGS. 3 and 4, the first or second filter wall 21, 22 may be formed from a layer of flexible sheet material overlapped upon itself around the inside or outside of at least one bend 30, 31. Thus the inside of each bend 30, 31 may be formed from two layers of the flexible sheet material forming the first filter wall 21 (as in the first bend 30 in FIG. 3) or second filter wall 22 (as in the second bend 31 in FIG. 3).

The ostomy appliance 10 may further comprise at least one gas filter element 40 located adjacent to the gas vent 15. The at least one gas filter element 40 may be located in the at least one filter channel 23, 24 adjacent to and overlying the filter channel outlet 27 as illustrated such that stomal gas must pass through the at least one gas filter element 40 to exit the filter channel outlet 27. In alternative embodiments the at least one gas filter element 40 may be located between the filter channel outlet 27 and gas vent 15 or may be mounted to the outside of the outer wall 12 over the gas vent 15. In the latter case the gas vent 15 may further comprise a filter cap (not shown) located over the at least one gas filter element 40. The at least one gas filter element 40 may be an odour filter or the like, for example a charcoal or activated carbon filter, to reduce the odour from the exiting stomal gas. The at least one gas filter element 40 may be a disc, which may be round, as illustrated. The diameter of the at least one gas filter element 40 may be at least about 10 mm, up to about 20 mm and/or may be about 15 mm.

As shown in FIG. 4 the filter arrangement 20 may further comprise at least one separation element 45, 46 extending at least partially along the at least one filter channel 23, 24, which may be for separating the first and second filter walls 21, 22 from one another along at least part of the at least one filter channel 23, 24. The at least one separation element 45, 46 is not shown in FIG. 3, 7A or 7B to ensure the first filter channel 23 is clearly identifiable.

The at least one separation element 45, 46 may substantially hinder or prevent stomal liquids and/or solids travelling along the at least one filter channel 23, 24. The at least one separation element 45, 46 may allow stomal gas to travel along the at least one filter channel 23, 24 and may comprise at least one separation element channel 47 for allowing such passage of stomal gas (see FIG. 8A). The filter arrangement 20 may comprise first and second separation elements 45, 46 located in each of the first and second filter channels 23, 24 respectively.

The or each separation element 45, 46 may extend around at least one bend 30, 31 and may extend at least between the first and second bends 30, 31, i.e. at least along the second channel section 36. The or each separation element 45, 46 may extend out of the at least one filter channel inlet 25, 26 as illustrated. The or each separation element 45, 46 may extend along at least about 50%, at least about 75% or at least about 85% of the length of the or each filter channel 23, 24 between the respective filter channel inlet 25, 26 and the filter channel outlet 27. In particular, the or each separation element 45, 46 may extend from the respective filter channel inlet 25, 26 and around the at least one bend 30, 31, preferably around both the first and second bends 30, 31, towards the filter channel outlet 27.

FIGS. 6A to 6F illustrate an exemplary method for forming the filter arrangement 20 illustrated in FIGS. 1, 2 and 4, including the at least one separation element 45 and first and second filter channels 23, 24 extending between the first and second filter walls 21, 22 around first and second bends 30, 31. Initially, as in FIG. 6A, the first and second filter walls 21, 22 may be cut from a flexible sheet material as V-shaped strips, the first and second separation elements 45, 46 may be formed as elongate strips and the at least one gas filter element 40 may be provided. The filter channel outlet 27 may be formed by cutting an aperture in the first filter wall 21. As in FIG. 6B, the first and second separation elements 45, 46 may be located on (and optionally attached to) the first filter wall 21 and the at least one gas filter element 40 may be mounted over the filter channel outlet 27. As in FIG. 6C, the second filter wall 22 may be located over the first filter wall 21, the first and second separation elements 45, 46 and the at least one gas filter element 40. At least one filter channel join or weld 70 may then be applied along the first and second channel edges 50, 51 to connect the first and second filter walls 21, 22. Prior to folding, the at least one filter channel 23, 24, and the channel sections 35, 36, 37 thereof, extend along a single axis and/or in series. As in FIGS. 6D and 6E, the first and second filter channels 23, 24 may be folded back upon themselves to form the first and second bends 30, 31 in each of the first and second filter channels 23, 24 and such that the first and second bends 30, 31 are at and between the channel section ends. As in FIG. 6F, an additional filter channel join or weld 71 may then be applied along the first and second channel edges 50, 51 to hold the filter arrangement 20 in its Z-shape.

Figure 7A:
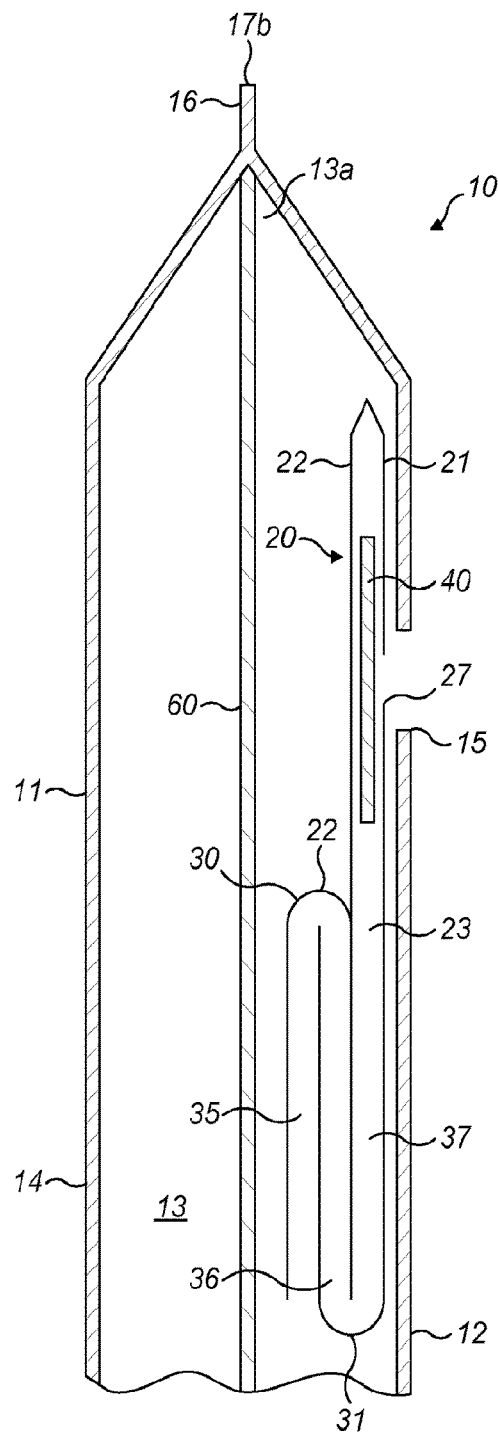
FIG. 7A is a cross-sectional view of the ostomy appliance of FIG. 1 through section B-B illustrating a further embodiment of the filter arrangement with a separation element of a filter arrangement hidden from view.
Figure 7B:
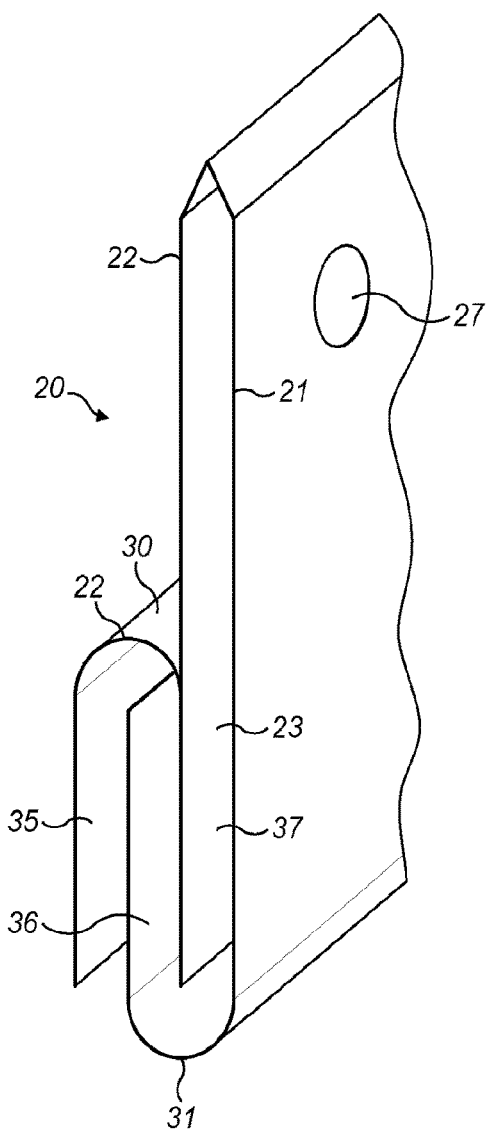
FIG. 7B is a perspective view of the filter arrangement of FIG. 6A with the separation element hidden from view.

Other constructions of the first and second filter walls 21, 22 and at least one bend 30, 31 extending between the first and second filter walls 21, 22 fall within the scope of the present disclosure. In alternative embodiments they may instead comprise multiple layers or strips located adjacent to one another along the at least one filter channel 23, 24. FIGS. 7A and 7B illustrate an embodiment in which the first and second filter walls 21, 22 are not formed of continuous strips of flexible sheet material. The inside of at least one bend 30, 31 may comprise a single layer of flexible sheet material forming one of the first and second filter walls 21, 22. This single layer may extend from the inside of and away from the at least one bend 30, 31 without being folded back upon itself. The outside of the at least one bend 30, 31 may comprise a layer of flexible sheet material folded back upon itself. For example, as in FIGS. 7A and 7B, the first filter wall 21 may comprise one strip of flexible sheet material and the second filter wall 22 may comprise two strips of flexible sheet material. The inside of the first bend 30 and outside of the second bend 31 may comprise the strip of the first filter wall 21. The outside of the first bend 30 may be formed from one strip of the second filter wall 22 and the inside of the second bend 30 may be formed from another strip of the second filter wall 22.

Figure 8A:
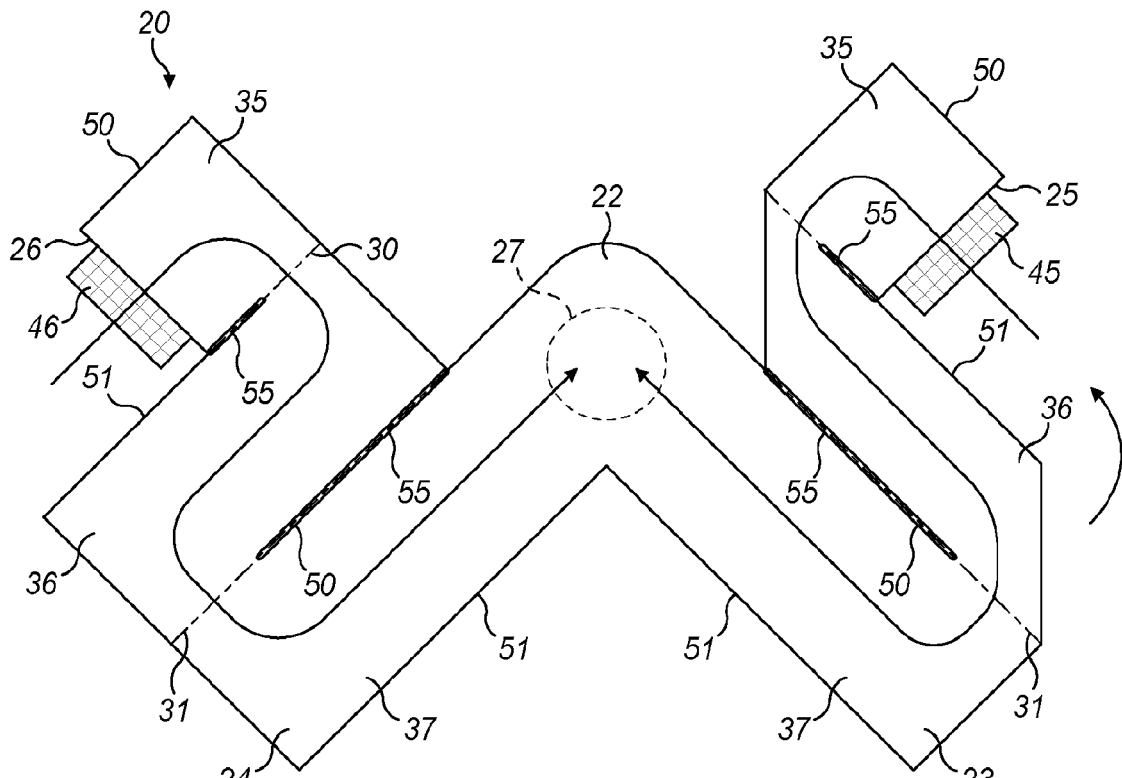
FIGS. 8A and 8B are perspective views illustrating an alternative method of forming the filter arrangements of FIGS. 1 to 5.
Figure 8B:
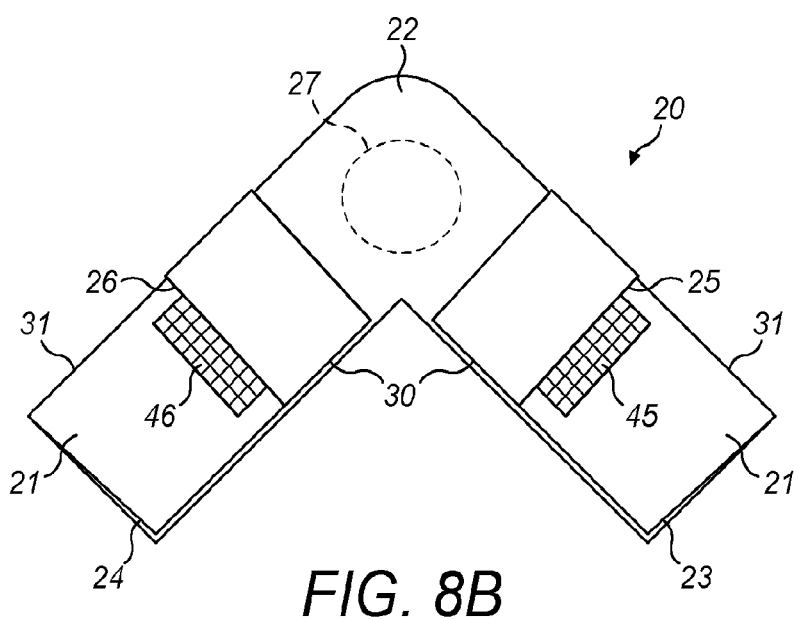

FIGS. 8A and 8B illustrate a further arrangement of the filter arrangement 20 similar to that shown in FIG. 1, including the at least one separation element 45 and first and second filter channels 23, 24 extending between the first and second filter walls 21, 22 around at least one bend 30, 31. The description above equally applies to FIGS. 8A and 8B and equivalent reference numerals have been used. However, rather than being between channel section ends as in FIGS. 3, 4 and 6A to 6F, the at least one bend 30, 31 is located at and between the channel edges 50, 51 of the channel sections 35, 36, 37. As a result, the fluid flow around the or each filter channel 23, 24 may extend around about 180 degrees around a single axis around the at least one bend 30, 31. Thus the fluid flow may change in direction about a two axes as it travels around the at least one bend 30, 31 between channel sections 35, 36, 37. In particular, the fluid flow may initially change about 90 degrees in direction about a first axis in order to reach the at least one bend 30, 31 at the channel edge 50, 51. The fluid flow may subsequently change about 180 degrees around a second axis, which may be perpendicular to the first axis and parallel to the main direction of fluid flow in the channel sections 35, 36, 37. As in FIGS. 8A and 8B, the or each filter channel 23, 24 may therefore still extend between the first and second filter walls 21, 22 around first and second bends 30, 31 such that the or each filter channel 23, 24 is Z-shaped and/or has a tortuous path.

In particular, the first channel section 35 may extend between first channel section ends, the filter channel inlet 25, 26 being located at a first channel section end and the first bend 30 being located at a first channel section edge 51 (which may be adjacent to, but not around, an opposing first channel section end). The second channel section 36 may extend between second channel section ends, the first bend 30 being located at a second channel section edge 51 (which may be adjacent to, but not around a second channel section end) and the second bend 31 may be located at the opposing second channel edge 50 (which may be located adjacent to, but not around, the opposing second channel section end). The third channel section 37 may extend between third channel section ends, the second bend 31 being located at a third channel section edge 50 (which may be located adjacent to, but not around, a third channel section end) and the filter channel outlet 27 being located at the opposing third channel section end.

FIG. 8A illustrates the folds required to form such an arrangement. Prior to folding, the channel sections 35, 36, 37 extend adjacent and parallel to one another. Channel section edge welds, joins and/or heat seals 55 may be applied between the first and second filter walls 21, 22 to form the separate channel sections 35, 36, 37. The at least one filter channel 23, 24 may be folded back upon itself at least once to form the at least one bend 30, 31 between channel section edges 50, 51 of the channel sections 35, 36, 37. In particular, the first and second channel sections 35, 36 may be folded over each other about a channel section edge 51 to form the first bend 30. The second and third channels sections 36, 37 may be folded over each other about a channel section edge 50 to form the second bend 31.

Figure 9A:
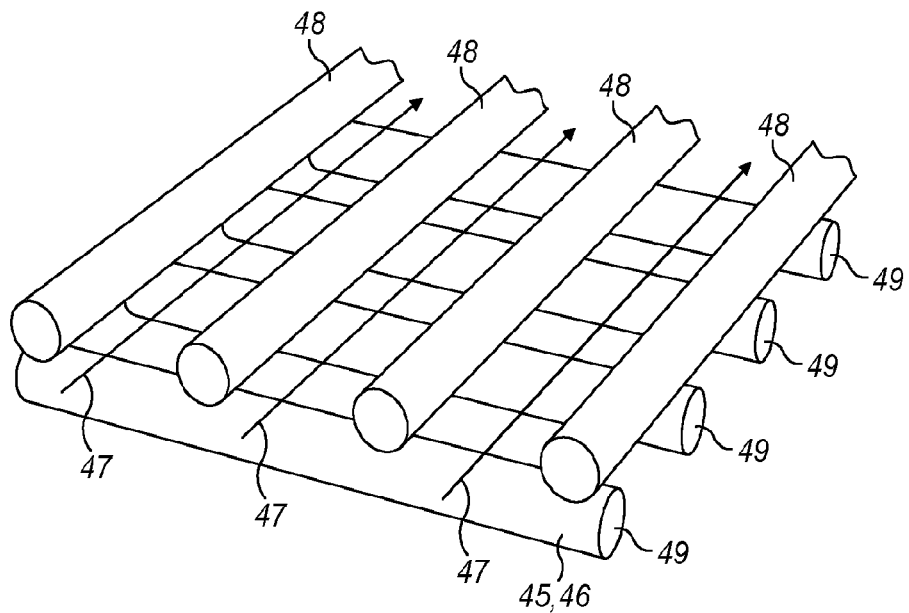
FIG. 9A is a perspective view of an embodiment of a separation element of the ostomy appliance illustrated in FIG. 1.
Figure 9B:
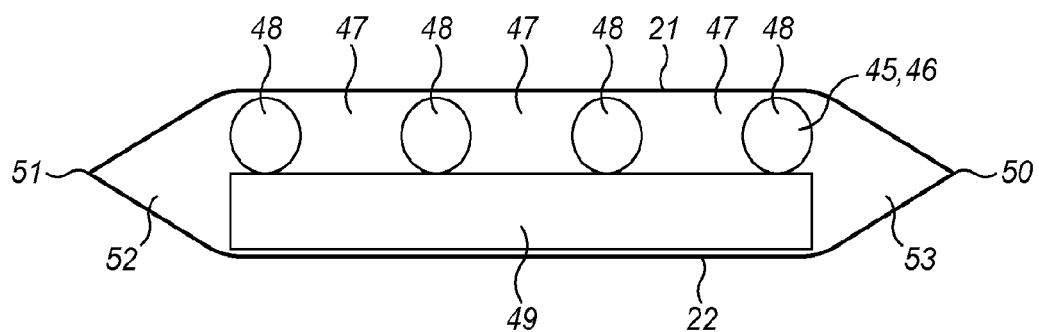
FIG. 9B is a cross-sectional view across the width of a filter channel of the filter arrangement of the ostomy appliance of FIG. 1 comprising the separation element of FIG. 10.

As illustrated in further detail in FIGS. 9A and 9B, the at least one separation element 45, 46 may comprise a mesh 45, 46. The mesh 45, 46 may be substantially hard and/or non-compressible to maintain the separation between the first and second filter walls 21, 22 and may be sufficiently flexible such that it bends around the at least one bend 30, 31. The mesh 45, 46 may comprise a plurality of wefts 48 and warps 49, which may be arranged in a regular array and may comprise openings therebetween. The wefts 48 and warps 49 may overlie one another as illustrated, may be interlinked or may be in the form of a grid with a continuous thickness. In particular, the mesh 45, 46 may not be a nonwoven material, may not be an irregularly woven material, may not be an open celled material and may not be a foam.

The mesh 45, 46 may comprise at least one separation element channel 47 therealong for stomal gas to pass through the mesh 45, 46 to the filter channel outlet 27. The at least one separation element channel 47 may extend continuously along the entire mesh 45, 46 to provide a clear stomal gas path therethrough. The at least one separation element channel 47 may be formed between adjacent warps 49 or between adjacent wefts 48 of the mesh 45, 46 as illustrated, particularly if the wefts 48 all overlie the warps 49 and vice-versa. In particular, a plurality of separation elements channels may be formed between a plurality of adjacent wefts 48 as illustrated, the wefts 48 extending along the at least one filter channel 23, 24. In this regard, the terms warps 49 and wefts 48 are merely used for nomenclature and are interchangeable.

As illustrated in FIG. 9B, the at least one separation element 45 may be separated from the channel edges 50, 51 by at least one separation element gap 52, 53. The at least one separation element gap 52, 53 may provide a further path for stomal gas to travel along the at least one filter channel 23, 24.

The mesh 45, 46 may be at least about 10 mm wide, up to about 20 mm wide and/or may be about 15 mm wide. The mesh 45, 46 may be at least about 60 mm long, up to about 100 mm long and/or may be about 80 mm long. The mesh 45, 46 may extend out of the at least one filter channel inlet 25, 26 by at least about 1 mm, by up to about 10 mm and/or by about 5 mm. The at least one separation element gap 52, 53 may be at least about 1 mm wide (i.e. at least 1 mm between the mesh 45, 46 and channel edge 50, 51), may be up to about 5 mm wide and/or may be about 3.5 mm wide.

The present disclosure further provides an ostomy appliance 10 and filter arrangement 20 in which the filter arrangement 20 may comprise the at least one separation element 45, preferably in the form of the mesh 45, 46, and may not comprise the at least one filter channel 23, 24 extending between the first and second filter walls 21, 22 around at least one bend 30, 31. Instead, the filter arrangement 20 may comprise a tortuous or Z-shaped path formed differently or without such a path. FIGS. 10A to 12B illustrate suitable embodiments in accordance with the present disclosure. Similar features are illustrated with similar reference numerals to those used in FIGS. 1 to 9B.

Figure 10A:
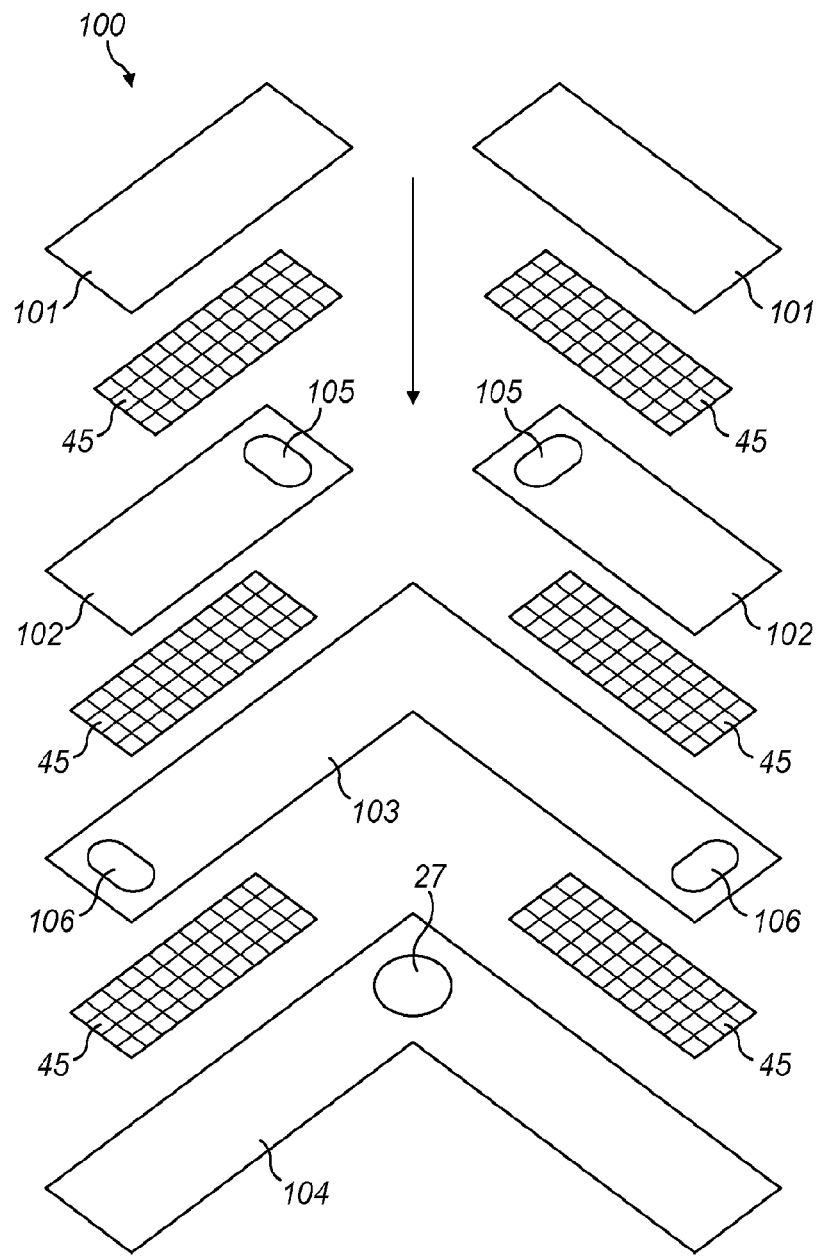
FIGS. 10A and 10B are perspective views illustrating a further embodiment of a filter arrangement in exploded and formed configurations respectively in accordance with the present disclosure.
Figure 10B:
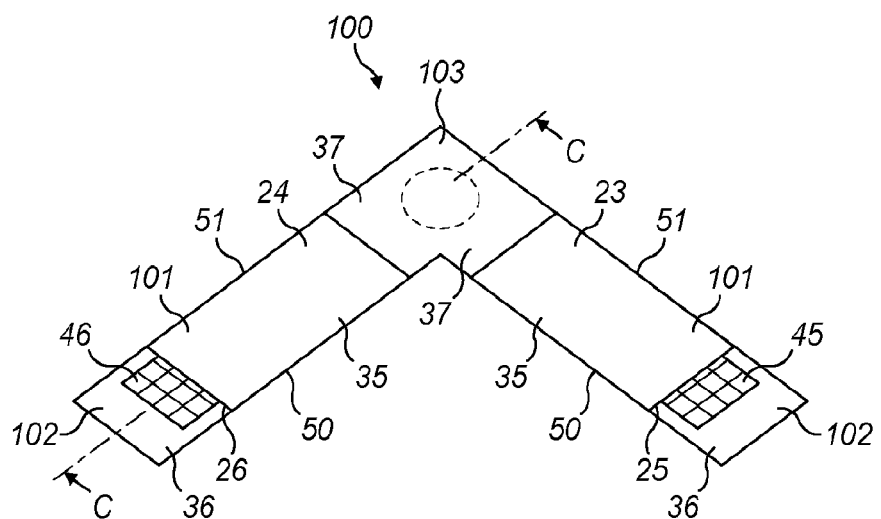
Figure 10C:
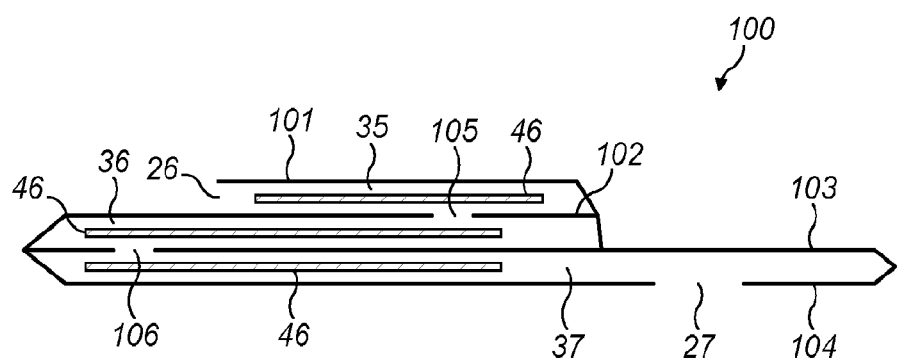
FIG. 10C is a cross-sectional view through section C-C of the filter arrangement shown in FIG. 10B.

FIGS. 10A to 10C illustrate a filter arrangement 100 comprising a tortuous path without at least one bend 30, 31 between first and second filter walls 21, 22 and at least one separation element 45, 46, such as in the form of a mesh 45, 46. As illustrated, the filter arrangement 100 comprises a plurality of filter walls 101, 102, 103, 104 overlying one another to form the at least one filter channel 23, 24 with a plurality of channel sections 35, 36, 37 therebetween. The channel sections 35, 36, 37 are fluidly connected by at least one aperture 105, 106 through the filter walls 102, 103. Thus stomal gas may travel through the at least one filter channel inlet 25, 26 to the filter channel outlet 27 by travelling along the at least one filter channel 23, 24, through the mesh 45, 46 and through the aperture(s) 105, 106.

The filter arrangement 100 may comprise a first channel section 35 formed between a first filter wall 101 and a second filter wall 102 and extending from at least one filter channel inlet 25, 26 to a first aperture 105 in the second filter wall 102. The filter arrangement 100 may comprise a second channel section 36 formed between the second filter wall 102 and a third filter wall 103 and extending from the first aperture 105 to a second aperture 106 in the third filter wall 103. The filter arrangement 100 may comprise a third channel section 37 formed between the third filter wall 103 and a fourth filter wall 104 and extending from the second aperture 106 to the filter channel outlet 27. The first, second, third and fourth filter walls 101, 102, 103, 104 may each be formed from separate layers of flexible sheet material and may be welded together at their edges 50, 51. The third and fourth filter walls 103, 104 of each of the first and second filter channels 23, 24 may be formed from the same layers of material as illustrated in FIG. 10A. The first and second filter walls 101, 102 of each of the first and second filter channels 23, 24 may each be formed from different layers of material.

A separation element 45, 46 may be located in at least one, preferably each, channel section 35, 36, 37. The or each separation element 45, 46 may be formed in any manner as discussed above and is preferably a mesh 45, 46. It may, in particular, comprise the at least one separation element channel 47 for providing a clear path for stomal gas to pass along each of the first and second filter channels 23, 24.

Figure 11A:
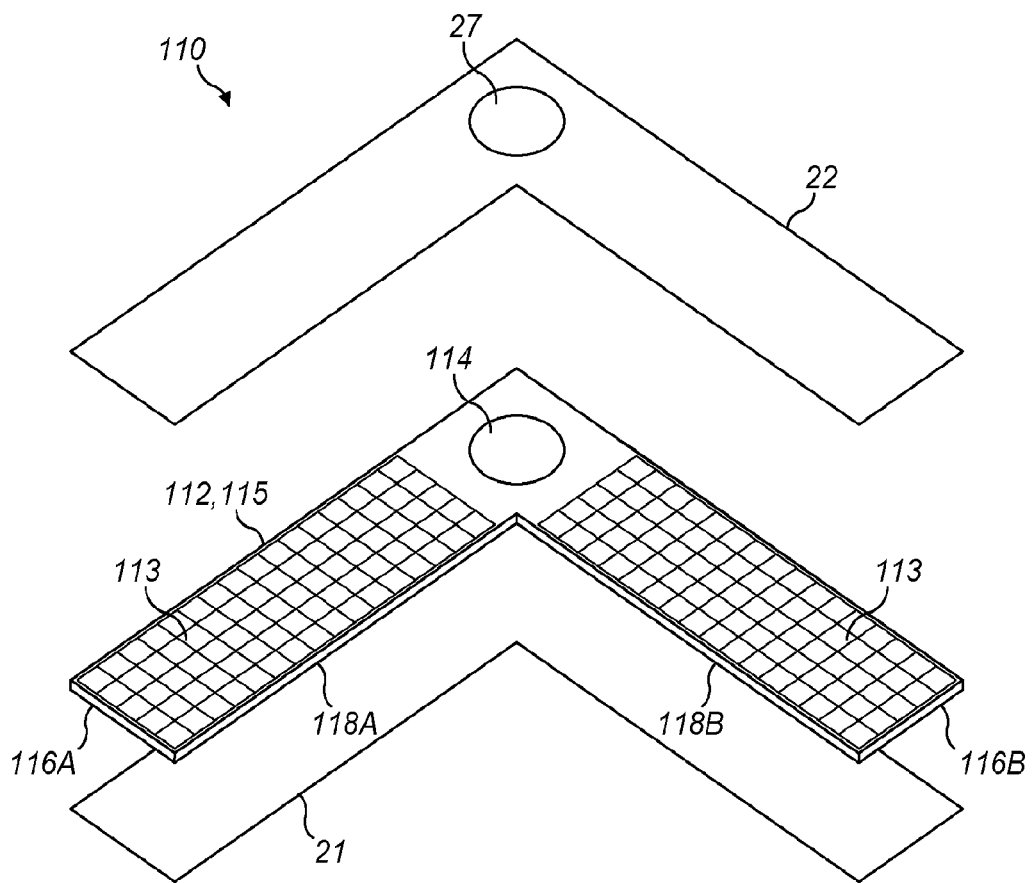
FIGS. 11A and 11B are perspective views illustrating a further embodiment of a filter arrangement in exploded and formed configurations respectively in accordance with the present disclosure.
Figure 11B:
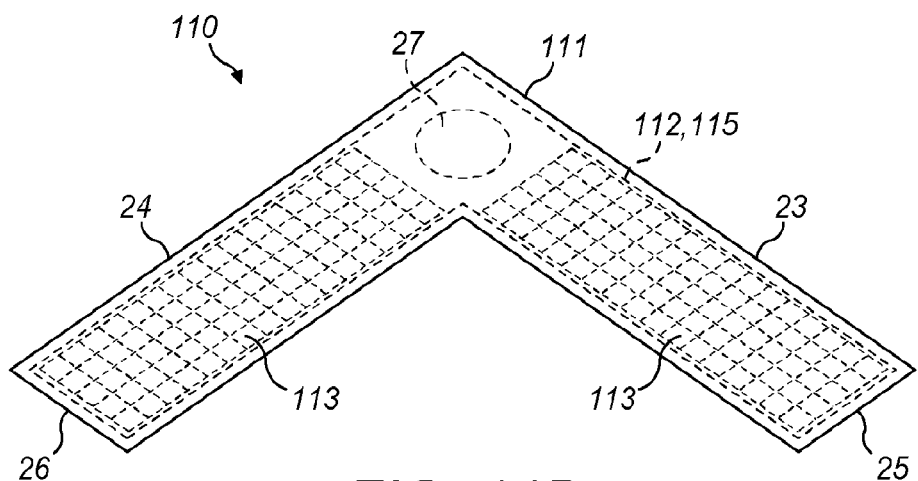

FIGS. 11A and 11B illustrate a further embodiment of the filter arrangement 110 in which the at least one filter channel 23, 24 may only comprise a single channel section 111 and in which a separation element 112 extends through the at least one filter channel 23, 24. In particular, each at least one filter channel 23, 24 extends from a filter channel inlet 25, 26 to the filter channel outlet 27 without passing around a bend. The separation element 112 may comprise a housing 115, which may be plastic, rigid, semi-rigid, hollow and/or injection moulded, and the housing 115 may be mounted in the first and/or second filter channel 23, 24. The separation element 112 may be located, preferably heat sealed or welded, between first and second filter walls 21, 22 as shown in FIG. 11B. The housing 115 may be "n" shaped and may extend along both filter channels 23, 24 and across the filter channel outlet 27. The housing 115 may comprise first and second housing inlets 116A, 116B and a housing outlet 114. The housing 115 may comprise first and second housing passageways 118A, 118B leading from the first and second housing inlet 116A, 116B respectively to the housing outlet 114.

The separation element 112 may comprise at least one mesh 113 located inside the housing 115, for example by insertion therein or by moulding, and preferably inside the first and/or second housing passageway 118A, 118B. The at least one mesh 113 may comprise a textile. The or each mesh 113 may extend along part of the housing 115 from the first and/or second housing inlet 116A, 116B. The housing outlet 114 may be aligned with the filter channel outlet 27.

In use, stomal fluid may flow through the filter channel inlet(s) 25, 26 and through the first and second housing inlets 116A, 116B into the housing 115. The stomal fluid may flow along the first and/or second housing passageways 118A, 118B via the mesh(es) 113, which may form a tortuous path for the stomal fluid such that the flow of stomal liquids and stomal solids is hindered whilst the stomal gas can flow therethrough. The stomal has may flow through the housing outlet 114 and out of the filter channel outlet 27 to the gas vent 15.

Figure 12A:
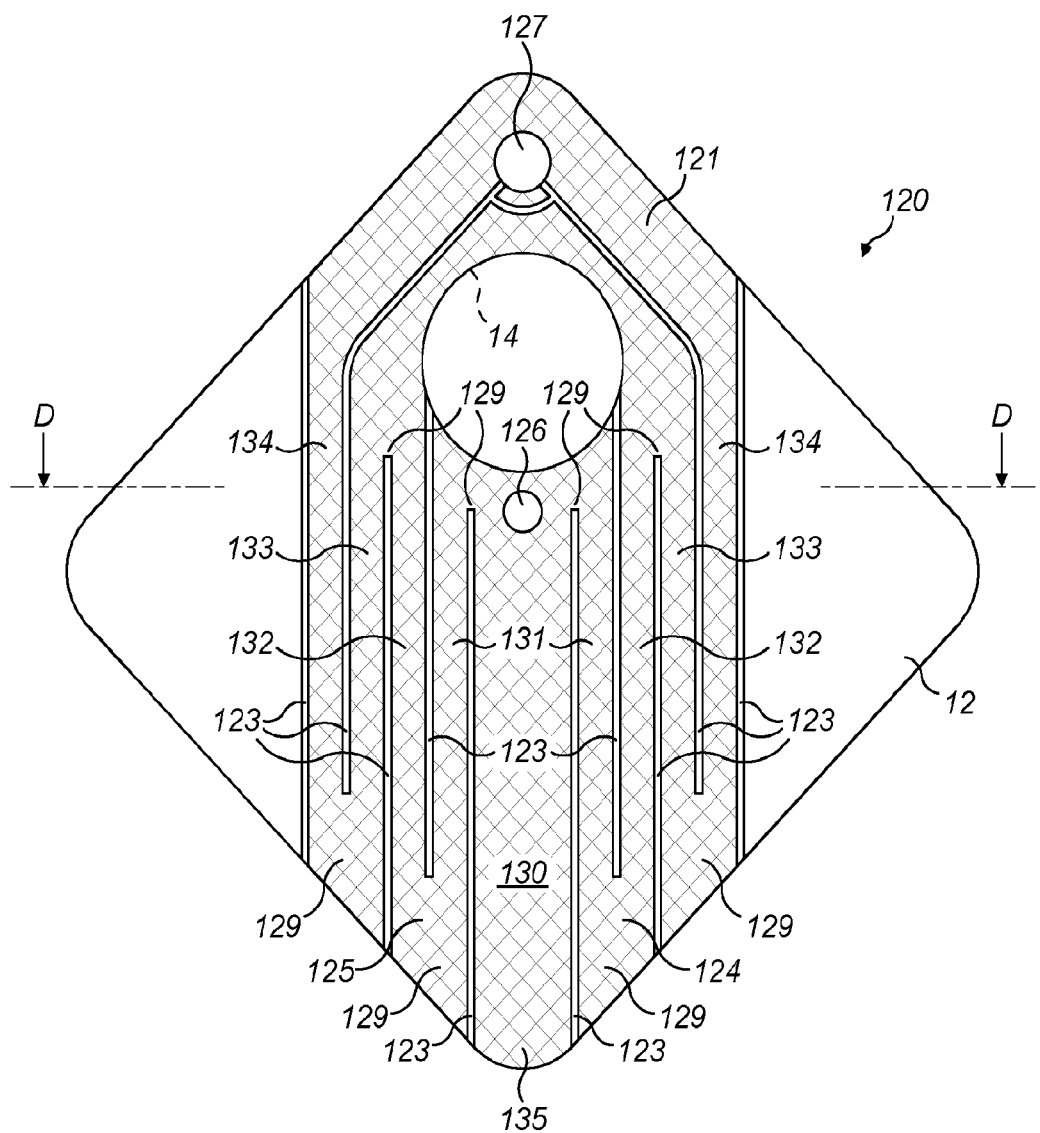
FIG. 12A is a plan view of a further embodiment of an ostomy appliance in accordance with the present disclosure.
Figure 12B:
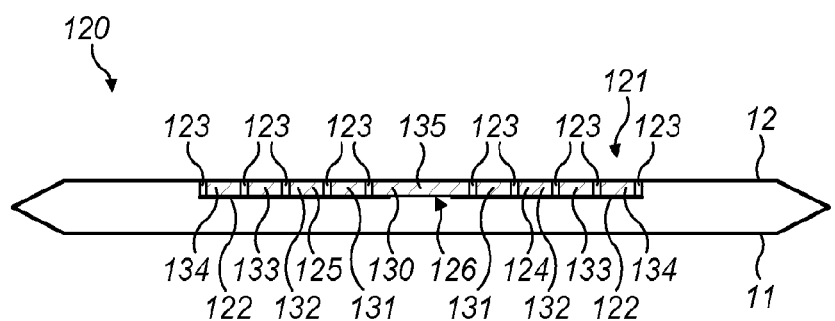
FIG. 12B is a cross-section view through section D-D of the ostomy appliance of FIG. 11A.

FIGS. 12A and 12B illustrate a further embodiment of the ostomy appliance 120 in accordance with the present disclosure comprising a filter arrangement 121 with a tortuous path. The filter arrangement 121 may comprise a filter wall 122 attached to the outer wall 12 by attachment lines 123 and the attachment lines 123 form at least one filter channel 124, 125, preferably first and second filter channels 124, 125 as illustrated. The attachment lines 123 may be formed by welding or any other suitable attachment method.

The at least one filter channel 124, 125 may extend tortuously (i.e. around at least one bend) from a filter channel inlet 126 to a filter channel outlet 127 at the gas vent 15. The at least one filter channel 124, 125 may extend between the filter wall 122 and outer wall 12. The at least one filter channel 124, 125 may comprise a plurality of filter channel sections 130, 131, 132, 133, 134, which may extend substantially parallel to one another and parallel to the planes of the filter and outer walls 122, 12. They may extend substantially parallel to a centreline defined between the top and bottom of the ostomy appliance 120. The filter channel sections 130, 131, 132, 133, 134 may be partially separated from each other by the attachment lines 123 and may be in fluid communication with each other by gaps 129 between the outer and filter walls 12, 122. Thus the fluid flowing through the at least one filter channel 124, 125 may tortuously pass repeatedly upwardly and downwardly when passing between the filter channel inlet 126 and filter channel outlet 127.

The filter arrangement 121 may comprise at least one separation element 135, which may be a mesh as illustrated, extending through the at least one filter channel 124, 125. The filter arrangement 121 may comprise a separation element 135 extending across a plurality of filter channel sections 130, 131, 132, 133, 134 as illustrated. The attachment lines 123 may pass through the at least one separation element 135 such that it is also attached to the outer and filter walls 12, 122. For example, the at least one separation element 135 may be welded to the outer and filter walls 12, 122.

The ostomy appliance 10 may comprise a shield wall 60 extending partially between the inner and outer walls 11, 12 and arranged to extend across, overlap, be aligned with and be directly adjacent to the stomal inlet 14. The shield wall 60 may direct stomal output received from the stomal inlet 14 downwardly into the cavity 13 and towards the cavity lower end 13b. The shield wall 60 may comprise a substantially impermeable region 65 opposite and entirely overlapping the stomal inlet 14 such that stomal output cannot pass directly through the shield wall 60 after entering the cavity 13 by the stomal inlet 14. The surface area of the impermeable region 65 may entirely cover and/or may be at least, preferably at least 110% of, the area of the stomal inlet 14.

The shield wall 60 may be located between the inner wall 11 and the filter arrangement 20 as illustrated. The shield wall 60 may extend across about the upper half of the cavity 13, inner wall 11 and outer wall 12. The shield wall 60 may be substantially triangular in shape and thus have the same shape as upper portions of the inner and outer walls 11, 12. The edges of the shield wall 60 may extend from the upper apex 17a along the first and second edges 18a, 18b towards the opposed lateral apexes 17c, 17d.

The shield wall 60 may extend to a lower edge 64 separated from the cavity lower end 13b such that stomal output can pass between the lower edge 64 and cavity lower end 13b. The lower edge 64 may be straight and may extend between the first and second edges 18a, 18b. The lower edge 64 may extend to up to about 90% of the length between the cavity upper and lower ends 13a, 13b and may extend between about 25% and about 75% of the length of the inner wall 11 from the top of the ostomy appliance 10, the upper apex 17a and/or the cavity upper end 13a.

The shield wall 60 may be joined to the inner and outer walls 11, 12 at or adjacent to a part or the whole of their first and second edges 18a, 18b, preferably by use of joining, welding, adhesive or equivalent means. Welding is a preferred method of joining and the peripheral join that joins the inner and outer walls 11, 12 and shield wall 60 may be the whole or a portion of the peripheral joint 16 that joins the inner and outer walls 11, 12. As shown in FIG. 1, the peripheral joint 16 may extend around a full perimeter of the inner and outer walls 11, 12 and may extend around the top edges, namely first and second edges 18a, 18b, of the shield wall 60. The lower edge 64 of the shield wall 60 may be a free edge and may be moveable relative to the inner and/or outer walls 11, 12.

The shield wall 60 may comprise flexible sheet material in a similar manner to the at least one appliance wall 11, 12 and first and second filter walls 21, 22.

The shield wall 60 may comprise at least one shield wall aperture 61, 62 therethrough. The at least one shield wall aperture 61, 62 may be located adjacent to and not overlapping the stomal inlet 14. The at least one shield wall aperture 61, 62 preferably comprises first and second shield wall apertures 61, 62 on opposing sides of the impermeable region 65 (i.e. towards the opposed lateral apexes 17c, 17d). The or each at least one shield wall aperture 61, 62 may be triangular as illustrated and the hypotenuse of each of the first and second shield wall aperture 61, 62 may be directed towards each other as illustrated.

Figure 13A:
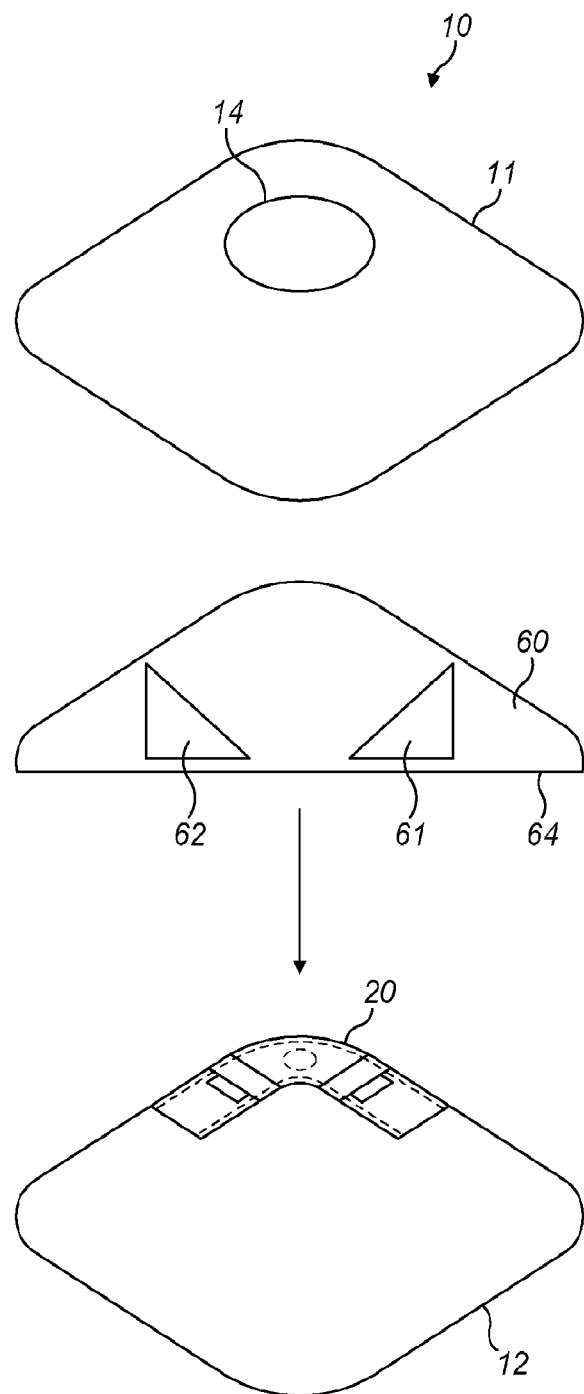
FIGS. 13A to 13C are perspective views illustrating the steps of forming the ostomy appliance of FIG. 1 comprising a shield wall.
Figure 13B:
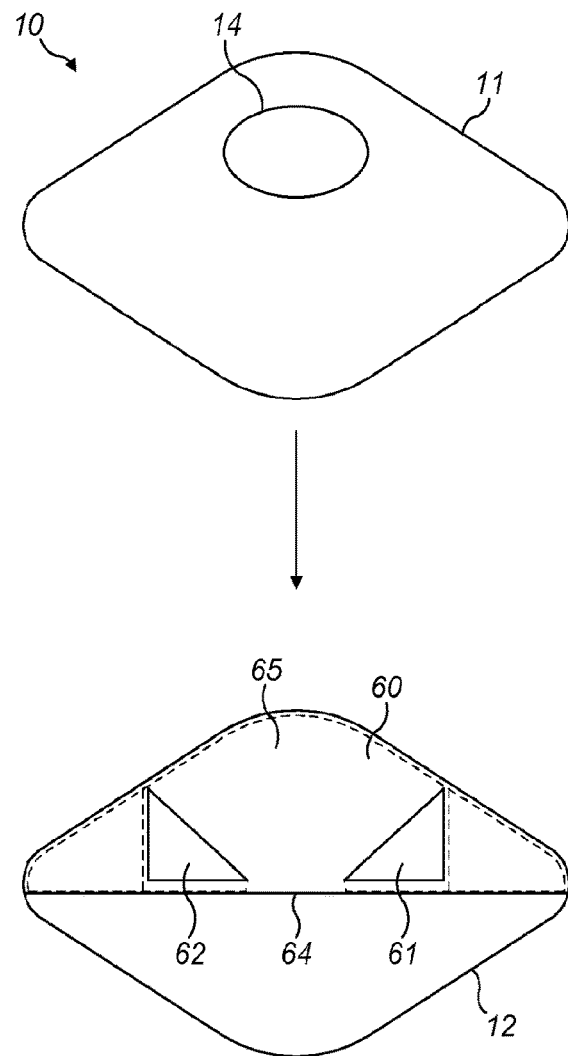
Figure 13C:
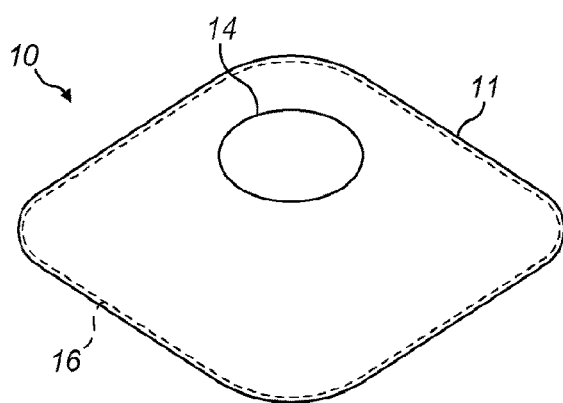

FIGS. 13A to 13C illustrate an exemplary method for forming the ostomy appliance 10 illustrated in FIGS. 1 to 4. As in FIG. 13A, the inner and outer walls 11, 12 may be formed from the flexible sheet material with the stomal inlet 14 and gas vent 15 therein. The shield wall 60 may be formed from the flexible sheet material with the first and second shield wall apertures 61, 62 therethrough. The filter arrangement 20 may be located and optionally attached to the outer wall 12. As in FIG. 13B, the shield wall 60 may be located over the filter arrangement 20 and outer wall 12 and attached thereto. As in FIG. 13C, the inner wall 11 may be mounted over the outer wall 12, filter arrangement 20 and shield wall 60 and then joined or welded thereto about the peripheral joint 16. Subsequently the wafer or coupling may be mounted over the stomal inlet 14. It will be appreciated that additional step may occur if other elements, such as separating walls, a drain or filters are also to be included in the ostomy appliance 10. Furthermore, it will be appreciated that the shield wall 60 may be attached to the inner wall 11 instead of or in addition to the outer wall 12.

Figure 15A:
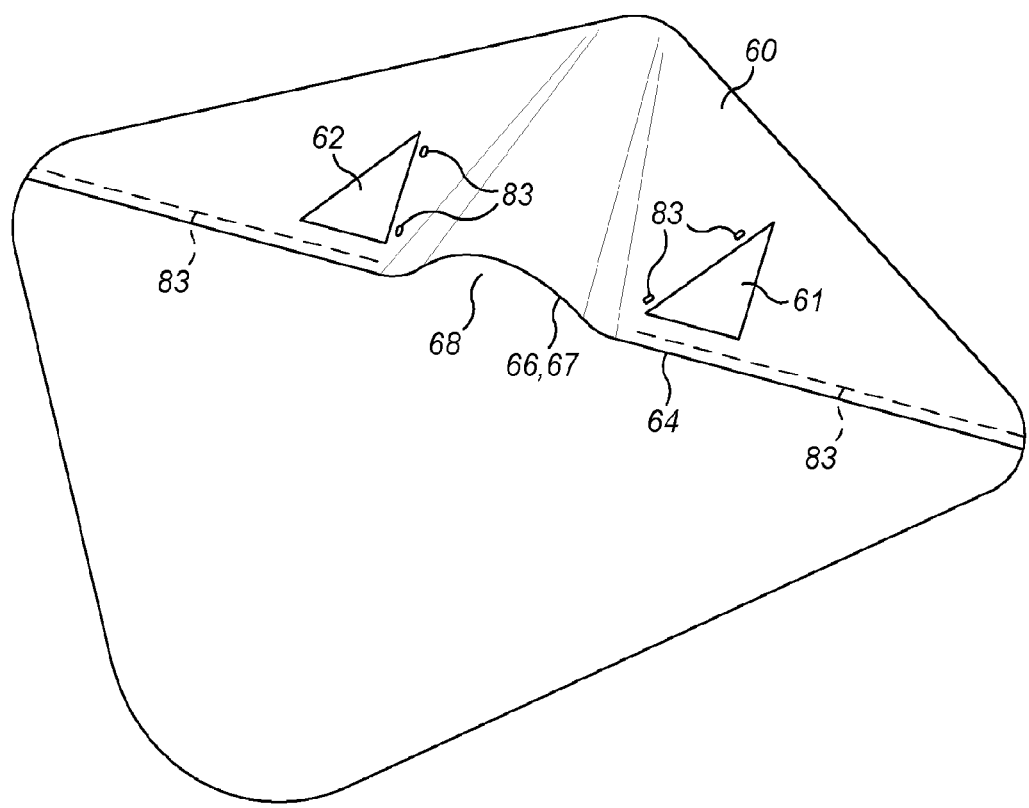
FIG. 15A is a perspective view of the outer and shield walls attached together as in FIG. 14C with a spacer arrangement illustrated.
Figure 15B:
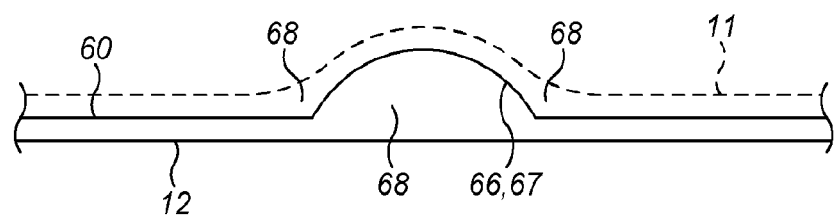
FIG. 15B is a partial cross-sectional view of the outer and shield walls attached together through section E-E of FIG. 14C with the location of an inner wall in the assembled ostomy appliance shown in broken lines for reference.

As illustrated in FIGS. 15A and 15B, the shield wall 60 may comprise a spacer arrangement 66 for at least partially separating the shield wall 60 from the inner and/or outer wall 11, 12 such that a fluid path 68, preferably a gas path, is formed between the inner wall 11 and shield wall 60 and/or between the shield wall 60 and outer wall 12. The fluid path 68 may lead from the stomal inlet 14 to the lower edge 64 and/or from the lower edge 64 to the at least one filter channel inlet 25, 26. Such a fluid path 68 may be formed by the shield wall 60 being attached such that it is at least partially separated from the outer wall 12, particularly when in the flat configuration.

The spacer arrangement 66 may comprise at least one undulation 67 of the flexible sheet material of the shield wall 60, as illustrated in FIGS. 15A and 15B. Thus the shield wall 60 may be mounted to the inner and/or outer wall 11, 12 such that they are at least partially not aligned parallel to one another. In particular, the at least one undulation 67 may be in the form of a region of excess flexible sheet material of the shield wall 60 relative to the overlapping region of the inner and/or outer wall 11, 12. Thus the region of excess flexible sheet material may form space between the shield wall 60 and the inner and/or outer wall 11, 12 and the space may form the fluid path 68. The at least one undulation 67 may form the fluid path 68 extending adjacent to the shield wall 60 to the at least one filter channel inlet 25, 26.

In particular, the shield wall 60 may comprise flexible sheet material extending across a shield wall area. The shield wall area may be considered to be the area of the shield wall 60 within the outer perimeter of the shield wall 60; thus the area of the at least one shield wall aperture 61, 62 is included in the shield wall area. The shield wall 60 may overlap the inner and/or outer wall 11, 12 across an overlap area of the inner and/or outer wall 11, 12. The shield wall area may be greater than the overlap area such that the at least one undulation 67 is formed by a region of excess flexible sheet material of the shield wall 60 relative to the overlapping region of the inner and/or outer wall 11, 12. Thus the footprint of the shield wall 60 may be the same as the overlap area, but the shield wall 60 may extend over a greater area than the overlap area.

The thickness of the flexible sheet material of the shield wall 60 may be constant across the at least one undulation 67. Therefore, the spacer arrangement 66 may not comprise anything other than the flexible sheet material forming the shield wall 60.

Figure 14A:
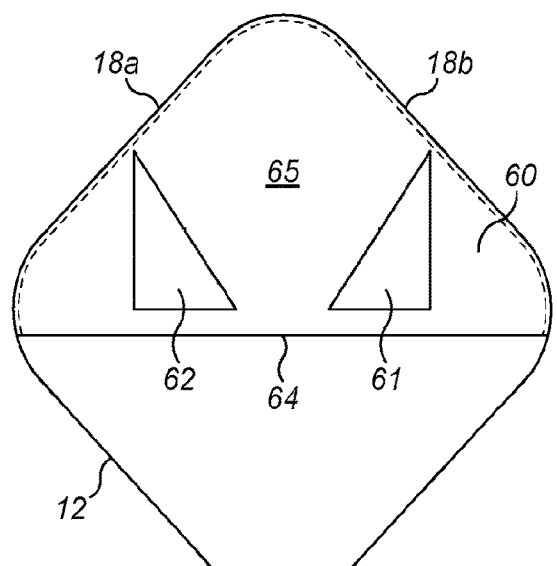
FIGS. 14A to 14C are plan views illustrating the steps of attaching the shield wall of FIGS. 13A to 13C to an outer wall of the ostomy appliance.
Figure 14B:
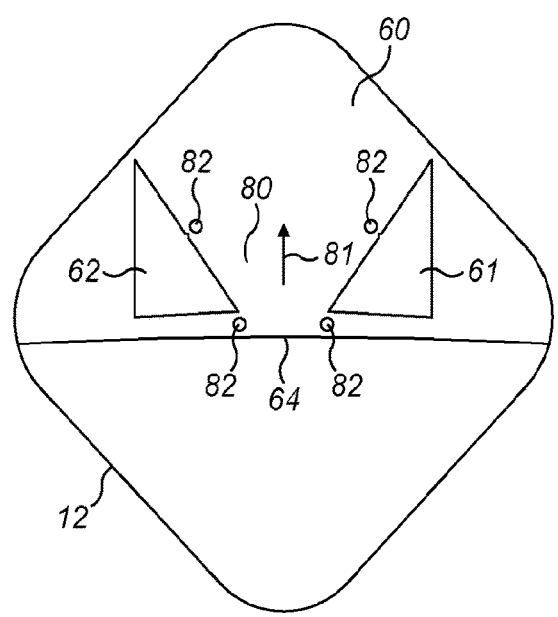
Figure 14C:
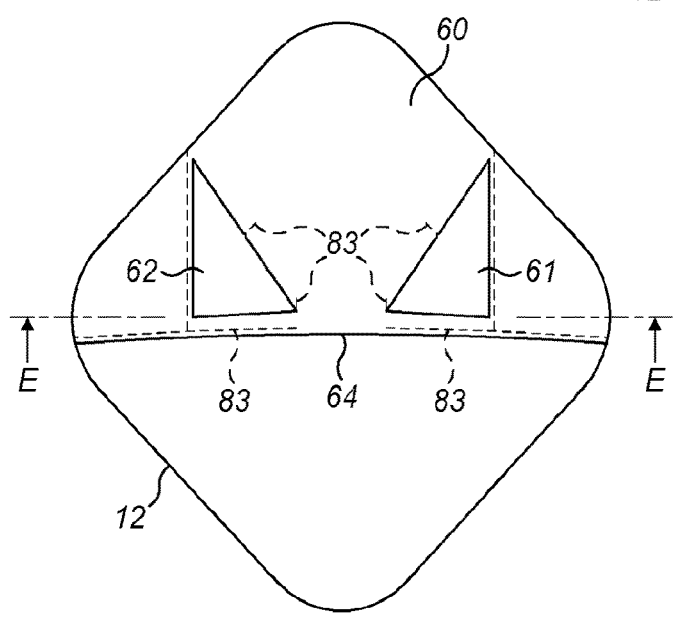

FIGS. 14A to 14C illustrate a preferred method of attaching the shield wall 60 to the inner and/or outer wall 12 such that the fluid path 68 is formed therebetween, particular such that stomal gas can reach the at least one filter channel inlet 25, 26. Preferably, as illustrated, the at least one undulation 67 is formed during the attachment of the shield wall 60 to the inner and/or outer wall 11, 12.

Initially, the shield wall 60 may be located over, and may be at least partially attached to, the inner or outer wall 11, 12. Prior to attachment, the flexible sheet material of the shield wall 60 may extend across a substantially flat plane prior to forming the at least one undulation 67. As in FIG. 14A, the shield wall 60 may be located over the outer wall 12 and may be partially attached to the outer wall 12, preferably along the first and second edges 18a, 18b.

Subsequently, at least one undulation 67 in the shield wall 60 may be formed. Forming the at least one undulation 67 may comprise bringing at least part of the flexible sheet material of the shield wall 60 out of the flat plane. For example, as in FIG. 14B, a central part 80 of the shield wall 60 may then be moved upwardly 81 relative to the outer wall 12 by moving contact points 82 upwards. The central part 80 may extend from the lower edge 64 between the first and second shield wall apertures 61, 62 and may substantially correspond to the impermeable region 65. As a result, an excess of material of the shield wall 60 relative to the outer wall 12 may be formed.

Subsequently, the shield wall 60 may be attached to the inner and/or outer wall 11, 12 to maintain the at least one undulation 67 in the shield wall 60. For example, as in FIG. 14C, the excess of material may be permanently incorporated into the shield wall 60 by joining it further to the outer wall 12. For example, at least one central part join 83 may be formed between the shield and outer walls 60, 12 around the central part 80, around the first and second shield wall apertures 61, 62 and/or along the lower edge 64.

The invention claimed is:

1. An ostomy appliance comprising:
   at least one appliance wall of flexible sheet material forming a cavity for containing a stomal output comprising stomal gas and stomal liquid and/or solids, the at least one appliance wall comprising a stomal inlet for receiving the stomal output and a gas vent for allowing the stomal gas to migrate out of the cavity; and
   a filter arrangement mounted to the at least one appliance wall and comprising:
      at least one filter channel extending from at least one filter channel inlet to a filter channel outlet, wherein the at least one filter channel inlet is located in the cavity for receiving the stomal output from the cavity and the filter channel outlet is mounted in communication with the gas vent for allowing stomal gas to migrate out of the at least one filter channel to the gas vent; and
      at least one separation element extending at least partially along the at least one filter channel for maintaining the at least one filter channel in an open configuration along at least part of the at least one filter channel for allowing stomal gas to pass therethough;
   wherein the at least one separation element comprises at least one mesh;
   wherein the at least one separation element comprises at least one separation element channel therealong for stomal gas to pass through the at least one separation element to the filter channel outlet;
   wherein the at least one separation channel is formed between adjacent warps or adjacent wefts of the at least one mesh.

2. An ostomy appliance as claimed in claim 1 wherein the mesh comprises a regular array of wefts and warps.

3. An ostomy appliance as claimed in claim 1, wherein the at least one separation element extends around at least one bend of the at least one filter channel.

4. An ostomy appliance as claimed in claim 1, wherein filter arrangement comprises first and second filter walls of flexible sheet material forming the at least one filter channel and wherein the at least one filter channel extends between the first and second filter walls around at least one bend for restricting the passage of stomal liquid and/or solids along the at least one filter channel.

5. An ostomy appliance as claimed in claim 1, wherein the filter arrangement comprises filter walls overlying one another to form the at least one filter channel, channel sections being formed between the filter walls, wherein the channel sections are fluidly connected by at least one aperture through the filter walls.

6. An ostomy appliance as claimed in claim 1 wherein the at least one separation element comprises a hollow housing and at least one mesh located in and extending along at least part of the housing, wherein the hollow housing extends from at least one housing inlet to at least one housing outlet, the at least one housing outlet being aligned with filter channel outlet.

7. An ostomy appliance as claimed in claim 1 wherein the at least one filter channel extends tortuously between a filter wall and the at least one appliance wall and comprises a plurality of filter channel sections partially separated from each other by attachment lines between the filter wall and the at least one appliance wall.

8. An ostomy appliance as claimed in claim 1, wherein the at least one appliance wall comprises inner and outer walls and further comprising a shield wall extending partially between the inner and outer walls and arranged to overlap the stomal inlet.

9. An ostomy appliance as claimed in claim 1, further comprising a selectively openable drain for allowing the stomal output to be selectively drained from the cavity or wherein the cavity is sealed within the ostomy appliance other than via the gas vent and the stomal inlet.

10. An ostomy appliance as claimed in claim 1, further comprising a wafer non-releasably attached to the at least one appliance wall around the stomal inlet or a releasable coupling attached to the at least one appliance wall around the stomal inlet and a wafer attached to the releasable coupling.

11. An ostomy appliance comprising:
    at least one appliance wall of flexible sheet material forming a cavity for containing a stomal output comprising stomal gas and stomal liquid and/or solids, the at least one appliance wall comprising a stomal inlet for receiving the stomal output and a gas vent for allowing the stomal gas to migrate out of the cavity; and
    a filter arrangement mounted to the at least one appliance wall and comprising:
       at least one filter channel extending from at least one filter channel inlet to a filter channel outlet, wherein the at least one filter channel inlet is located in the cavity for receiving the stomal output from the cavity and the filter channel outlet is mounted in communication with the gas vent for allowing stomal gas to migrate out of the at least one filter channel to the gas vent; and
       at least one separation element extending at least partially along the at least one filter channel for maintaining the at least one filter channel in an open configuration along at least part of the at least one filter channel for allowing stomal gas to pass therethough;
    wherein the filter arrangement comprises filter walls overlying one another to form the at least one filter channel, channel sections being formed between the filter walls, wherein the channel sections are fluidly connected by at least one aperture through the filter walls;
    wherein the filter arrangement comprises a first channel section formed between a first filter wall and a second filter wall and extending from the at least one filter channel inlet to a first aperture in the second filter wall, and a second channel section formed between the second filter wall and a third filter wall and extending from the first aperture to a second aperture in the third filter wall.

12. An ostomy appliance as claimed in claim 11 wherein the at least one separation element comprises at least one mesh that comprises a regular array of wefts and warps.

13. An ostomy appliance as claimed in claim 11 wherein the at least one separation element extends around at least one bend of the at least one filter channel.

14. An ostomy appliance as claimed in claim 11 wherein the first and second filter walls comprise flexible sheet material forming the at least one filter channel and wherein the at least one filter channel extends between the first and second filter walls around at least one bend for restricting the passage of stomal liquid and/or solids along the at least one filter channel.

15. An ostomy appliance as claimed in claim 11, wherein the at least one separation element comprises a hollow housing and at least one mesh located in and extending along at least part of the housing, wherein the hollow housing extends from at least one housing inlet to at least one housing outlet, the at least one housing outlet being aligned with filter channel outlet.

16. An ostomy appliance as claimed in claim 11, wherein the at least one filter channel extends tortuously between a filter wall and the at least one appliance wall and comprises a plurality of filter channel sections partially separated from each other by attachment lines between the filter wall and the at least one appliance wall.

17. An ostomy appliance as claimed in claim 11, wherein the at least one appliance wall comprises inner and outer walls and further comprising a shield wall extending partially between the inner and outer walls and arranged to overlap the stomal inlet.

18. An ostomy appliance as claimed in claim 11, further comprising a wafer non-releasably attached to the at least one appliance wall around the stomal inlet or a releasable coupling attached to the at least one appliance wall around the stomal inlet and a wafer attached to the releasable coupling.

\* \* \* \* \*